(12) United States Patent
Dickhaut et al.

(10) Patent No.: US 10,149,477 B2
(45) Date of Patent: Dec. 11, 2018

(54) SUBSTITUTED PYRIMIDINIUM COMPOUNDS FOR COMBATING ANIMAL PESTS

(71) Applicant: BASF SE, Ludwigshafen (DE)

(72) Inventors: Joachim Dickhaut, Heidelberg (DE); Arun Narine, Mannheim (DE); Wolfgang von Deyn, Neustadt (DE); Raffael Koller, Zurich (CH); Jean-Yves Wach, Zurich (CH); Devendra Vyas, Mumbai (IN); Ashokkumar Adisechan, Navi Mumbai (IN); Harish Shinde, Pune (IN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/517,189

(22) PCT Filed: Oct. 6, 2015

(86) PCT No.: PCT/EP2015/072973
§ 371 (c)(1),
(2) Date: Apr. 6, 2017

(87) PCT Pub. No.: WO2016/055431
PCT Pub. Date: Apr. 14, 2016

(65) Prior Publication Data
US 2017/0295791 A1    Oct. 19, 2017

(30) Foreign Application Priority Data
Oct. 6, 2014    (IN) .......................... 3157/MUM/2014

(51) Int. Cl.
| | | |
|---|---|---|
| C07D 513/04 | (2006.01) | |
| C07D 495/04 | (2006.01) | |
| A01N 43/90 | (2006.01) | |
| A01N 43/02 | (2006.01) | |
| A01N 43/48 | (2006.01) | |
| C07D 487/04 | (2006.01) | |
| A01N 25/02 | (2006.01) | |
| A61K 31/513 | (2006.01) | |
| A61K 31/519 | (2006.01) | |

(52) U.S. Cl.
CPC ............ *A01N 43/90* (2013.01); *A01N 25/02* (2013.01); *A01N 43/02* (2013.01); *A01N 43/48* (2013.01); *A61K 31/513* (2013.01); *A61K 31/519* (2013.01); *C07D 487/04* (2013.01); *C07D 495/04* (2013.01); *C07D 513/04* (2013.01); *A01N 2300/00* (2013.01)

(58) Field of Classification Search
CPC .. C07D 495/04; C07D 513/04; A61K 31/519; A01N 43/90; A01N 43/54
USPC ....................... 544/278; 514/260.1
See application file for complete search history.

(56) References Cited

U.S. PATENT DOCUMENTS

| | | | |
|---|---|---|---|
| 3,296,272 A | 1/1967 | Johnston | |
| 3,325,503 A | 6/1967 | Bimber | |
| 2012/0122680 A1* | 5/2012 | Holyoke, Jr. | .......... A01N 43/78 504/100 |
| 2014/0213448 A1 | 7/2014 | Buysse et al. | |

FOREIGN PATENT DOCUMENTS

| | | |
|---|---|---|
| CN | 101715770 A | 6/2010 |
| CN | 102126994 A | 7/2011 |
| DE | 19650197 A1 | 6/1998 |
| DE | 10021412 A1 | 6/2001 |
| DE | 102005009458 A1 | 9/2006 |
| EP | 0141317 A2 | 5/1985 |
| EP | 0152031 A2 | 8/1985 |
| EP | 0226917 A1 | 7/1987 |
| EP | 0243970 A1 | 11/1987 |
| EP | 0256503 A2 | 2/1988 |
| EP | 0428941 A1 | 5/1991 |
| EP | 0532022 A1 | 3/1993 |
| EP | 1028125 A1 | 8/2000 |
| EP | 1035122 A1 | 9/2000 |
| EP | 1122244 A1 | 8/2001 |
| EP | 1201648 A1 | 5/2002 |
| JP | 2002316902 A | 10/2002 |
| WO | 9846608 A1 | 10/1998 |
| WO | 9914187 A1 | 3/1999 |
| WO | 9924413 A2 | 5/1999 |
| WO | 9927783 A1 | 6/1999 |
| WO | 0029404 A1 | 5/2000 |

(Continued)

OTHER PUBLICATIONS

International Preliminary Report on Patentability for PCT Patent Application No. PCT/EP2015/072973, dated Apr. 20, 2017, 8 pages.

(Continued)

*Primary Examiner* — Susanna Moore

(74) *Attorney, Agent, or Firm* — Armstrong Teasdale LLP

(57) ABSTRACT

Substituted pyrimidinium compounds of the general formula (I):

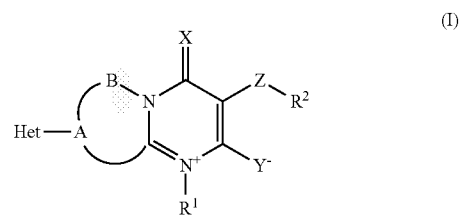

wherein the compounds are useful for controlling invertebrate pests.

14 Claims, No Drawings

(56) References Cited

FOREIGN PATENT DOCUMENTS

| | | |
|---|---|---|
| WO | 0046148 A1 | 8/2000 |
| WO | 0065913 A1 | 11/2000 |
| WO | 0154501 A2 | 8/2001 |
| WO | 0156358 A2 | 8/2001 |
| WO | 0222583 A2 | 3/2002 |
| WO | 0240431 A2 | 5/2002 |
| WO | 03010149 A1 | 2/2003 |
| WO | 03011853 A1 | 2/2003 |
| WO | 03014103 A1 | 2/2003 |
| WO | 03016286 A1 | 2/2003 |
| WO | 03016303 A1 | 2/2003 |
| WO | 03053145 A1 | 7/2003 |
| WO | 03061388 A1 | 7/2003 |
| WO | 03066609 A1 | 8/2003 |
| WO | 03074491 A1 | 9/2003 |
| WO | 2004049804 A2 | 6/2004 |
| WO | 2004083193 A1 | 9/2004 |
| WO | 2004094382 A1 | 11/2004 |
| WO | 2005063721 A1 | 7/2005 |
| WO | 2005077934 A1 | 8/2005 |
| WO | 2005087772 A1 | 9/2005 |
| WO | 2005087773 A1 | 9/2005 |
| WO | 2005120234 A2 | 12/2005 |
| WO | 2005123689 A1 | 12/2005 |
| WO | 2005123690 A1 | 12/2005 |
| WO | 2006015866 A1 | 2/2006 |
| WO | 2006043635 A1 | 4/2006 |
| WO | 2006087325 A1 | 8/2006 |
| WO | 2006087343 A1 | 8/2006 |
| WO | 2006089633 A2 | 8/2006 |
| WO | 2007006670 A1 | 1/2007 |
| WO | 2007043677 A1 | 4/2007 |
| WO | 2007082098 A2 | 7/2007 |
| WO | 2007090624 A2 | 8/2007 |
| WO | 2007101369 A1 | 9/2007 |
| WO | 2007101540 A1 | 9/2007 |
| WO | 2008067911 A1 | 6/2008 |
| WO | 2008134969 A1 | 11/2008 |
| WO | 2009090181 A2 | 7/2009 |
| WO | 2009099929 A1 | 8/2009 |
| WO | 2009124707 A2 | 10/2009 |
| WO | 2010006713 A2 | 1/2010 |
| WO | 2010018714 A1 | 2/2010 |
| WO | 2010034737 A1 | 4/2010 |
| WO | 2010060379 A1 | 6/2010 |
| WO | 2010069266 A1 | 6/2010 |
| WO | 2010069882 A1 | 6/2010 |
| WO | 2010127926 A1 | 11/2010 |
| WO | 2010129497 A1 | 11/2010 |
| WO | 2011017342 A2 | 2/2011 |
| WO | 2011017347 A2 | 2/2011 |
| WO | 2011017351 A2 | 2/2011 |
| WO | 2011028657 A1 | 3/2011 |
| WO | 2011069456 A1 | 6/2011 |
| WO | 2011077514 A1 | 6/2011 |
| WO | 2011085575 A1 | 7/2011 |
| WO | 2011135833 A1 | 11/2011 |
| WO | 2012000896 A2 | 1/2012 |
| WO | 2012029672 A1 | 3/2012 |
| WO | 2012034403 A1 | 3/2012 |
| WO | 2012034472 A1 | 3/2012 |
| WO | 2012084670 A1 | 6/2012 |
| WO | 2012136724 A1 | 10/2012 |
| WO | 2012143317 A1 | 10/2012 |
| WO | 2012168188 A1 | 12/2012 |
| WO | 2013003977 A1 | 1/2013 |
| WO | 2013007767 A1 | 1/2013 |
| WO | 2013010862 A1 | 1/2013 |
| WO | 2013024009 A1 | 2/2013 |
| WO | 2013024010 A1 | 2/2013 |
| WO | 2013047441 A1 | 4/2013 |
| WO | 2013047749 A1 | 4/2013 |
| WO | 2013050317 A1 | 4/2013 |
| WO | 2013055584 A1 | 4/2013 |
| WO | 2013092224 A1 | 6/2013 |
| WO | 2013127704 A1 | 9/2013 |
| WO | 2013129688 A1 | 9/2013 |
| WO | 2013162072 A1 | 10/2013 |
| WO | 2014036056 A1 | 3/2014 |
| WO | 2014090918 A1 | 6/2014 |
| WO | 2014126208 A1 | 8/2014 |
| WO | 2015038503 A1 | 3/2015 |

OTHER PUBLICATIONS

International Search Report issued in PCT/EP2015/072973 dated Apr. 14, 2016.
Written Opinion issued in PCT/EP2015/072973 dated Apr. 14, 2016.

* cited by examiner

SUBSTITUTED PYRIMIDINIUM COMPOUNDS FOR COMBATING ANIMAL PESTS

CROSS-REFERENCE TO RELATED APPLICATIONS

This application is a U.S. National Phase Application of PCT/EP2015/072973, filed Oct. 6, 2015, which claims the benefit of priority to IN Application No. 3157/MUM/2014, filed Oct. 6, 2014, the contents of which are hereby expressly incorporated by reference in their entirety.

The present invention relates to insecticidal substituted pyrimidinium compounds and/or to the compositions comprising such compounds for combating invertebrate pests. The invention also relates to pesticidal methods, to uses and to applications of substituted pyrimidinium compounds as described in the present invention and the stereoisomers, salts, tautomers and N-oxides thereof as well as compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the invention to provide compounds having a good pesticidal activity and showing a broad activity spectrum against a large number of different invertebrate pests, especially against difficult to control insects, arachnids and nematodes.

It has been found that these objectives can be achieved by substituted pyrimidinium compounds of the general formula (I), as defined below, including their stereoisomers, their salts, in particular their agriculturally or veterinary acceptable salts, their tautomers and their N-oxides.

Therefore, in a first aspect the present invention provides a substituted pyrimidinium compound of formula (I),

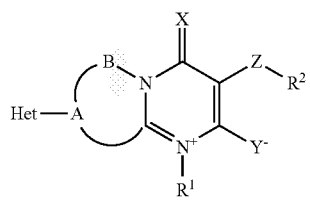

(I)

wherein

X, Y are each independently O or S;

Z is a direct bond, O, $S(O)_m$, $NR^b$, $C(R^{aa}R^{aa})O$, $C(=X^1)$, $C(=X^1)Y^1$ or $Y^1C(=X^1)$;

$X^1$ is O, S or $NR^b$;

$Y^1$ is O, S or $NR^c$;

A is CH or N, or, if part of a double bond, C, wherein the nitrogen of the pyrimidinium ring taken together with the contiguous linking carbon atom, B and A, as depicted in formula (I), form a four- to eight-membered ring, wherein each remaining ring member is selected from carbon atoms and up to 3 heteroatoms independently selected from up to 2 O, up to 2 S, and up to $3N(R^c)_p$, wherein up to 2 carbon atom ring members are independently selected from C(=O) and C(=S), and the sulfur atom ring members are independently selected from $S(=O)_m$, wherein each ring may be substituted with up to 3 $R^a$;

B is CR'R", $NR^b$, $S(O)_m$, O or, if part of a double bond, CR' or N;

R', R" is each independently H, halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^c$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$, or a three- to six-membered saturated, or partially unsaturated or aromatic carbo- or heterocyclic ring, which may contain 1 to 3 heteroatoms selected from $N$—$(R^c)_p$, O, and S which may be oxidized, and wherein the aforementioned groups and the carbo- or heterocyclic ring may be partially or fully substituted by R'";

R'" is each independently halogen, $C_1$-$C_6$-alkyl, $C_1$-$C_6$-haloalkyl, $C_1$-$C_6$-alkoxy or $C_1$-$C_6$-haloalkoxy; or R' and R" together form a group selected from =O, =S, $=CR^bR^c$, $=NR^c$, $=NOR^c$ and $=NNR^cR^c$ or, together with the carbon atom to which they are attached, form a three- to six-membered saturated or partially unsaturated carbo- or heterocyclic ring, which may contain 1 to 3 heteroatoms selected from $N$—$(R^c)_p$, O, and S which may have been oxidized, and wherein the afore-mentioned groups and the carbo- or heterocyclic ring may be partially or fully substituted by R'";

Het is a three- to ten-membered heterocyclic ring or a seven- to eleven-membered heterocyclic ring system, each ring or ring system member selected from carbon atoms and up to 4 heteroatoms independently selected from up to 2 O, up to 2 S, and up to $4N(R^c)_p$, wherein up to 3 carbon atom ring members are independently selected from C(=O) and C(=S) and the sulfur atom ring members are independently selected from $S(=O)_o(=NR^b)_q$, each ring or ring system optionally substituted with up to 5 $R^a$;

o, q are each independently 0, 1 or 2, provided that the sum (o+q) is 0, 1 or 2 for each ring;

$R^1$ is hydrogen, $C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl or $R^1$ may form a three- to eleven-membered saturated, partially unsaturated or aromatic carbo- or heterocyclic ring or ring system, which may contain 1 to 4 heteroatoms selected from $N(R^c)_p$, O, and S, wherein S may be oxidized, and wherein the aforementioned groups and the carbo- or heterocyclic ring system may be unsubstituted, partially or fully substituted by $R^a$; or $R^1$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^c$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, $S(=O)_o(=NR^b)_qR^c$ or $N=CR^bR^c$;

$R^a$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^c$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, Si(R$^d$)$_3$ or a three- to six-membered saturated, or partially unsaturated or aromatic carbo- or heterocyclic ring, which may contain 1 to 3 heteroatoms selected from N—(R$^c$)$_p$, O, and S which may be oxidized, and wherein the aforementioned groups and the carbo- or heterocyclic ring may be partially or fully substituted by R$^{aa}$, or two geminally bound groups R$^a$ together may form a group selected from =O, =S, =CR$^b$R$^c$, =NR$^c$, =NOR$^c$, and =NNR$^c$R$^c$;

R$^{aa}$ is each independently hydrogen, halogen, C$_1$-C$_6$-alkyl, C$_1$-C$_6$-haloalkyl, C$_1$-C$_6$-alkoxy or C$_1$-C$_6$-haloalkoxy;

R$^b$ is each independently hydrogen, C$_1$-C$_6$-alkyl, C$_1$-C$_6$-haloalkyl, C$_1$-C$_6$-alkoxy, C$_1$-C$_6$-haloalkoxy or a three- to six-membered saturated, or partially unsaturated or aromatic carbo- or heterocyclic ring, which may contain 1 to 3 heteroatoms selected from N(R$^c$)$_p$, O, and S, wherein S may be oxidized and which carbo- or heterocyclic ring may be partially or fully substituted by R$^{aa}$;

R$^c$ is each independently hydrogen, C$_1$-C$_4$-alkyl, C$_1$-C$_4$-haloalkyl, C$_1$-C$_4$-alkylcarbonyl, C$_1$-C$_6$ cycloalkyl, or a three- to six-membered saturated, partially unsaturated or aromatic carbo- or heterocyclic ring, which may contain 1 to 3 heteroatoms selected from N(R$^{aa}$)$_p$, O and S, wherein S may be oxidized and wherein the carbo- or heterocyclic ring may be partially or fully substituted by R$^{aa}$;

wherein two geminally bound groups R$^b$R$^b$, R$^c$R$^b$ or R$^c$R$^c$ together with the atom to which they are bound, may form a 3-, 4-, 5-, 6- or 7-membered saturated, partially unsaturated or aromatic carbo- or heterocyclic ring, which may contain 1 or 2 heteroatoms or heteroatoms groups selected from N, O, S, NO, SO and SO$_2$ and wherein the carbo- or heterocyclic ring may be partially or fully substituted by R$^{bb}$;

R$^{bb}$ is each independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, SF$_5$, OCN, SCN, Si(R$^d$)$_3$, C(=N(O)$_p$R$^b$)R$^b$, C(=NNR$^b$R$^c$)R$^b$, C(=NN(C(=O)O$_p$R$^c$)R$^b$)R$^b$, ON=CR$^b$R$^c$, ONR$^b$R$^c$, S(=O)$_o$(=NR$^b$)$_q$R$^c$, SO$_2$NR$^b$(=O)NR$^b$R$^c$, P(=X$^2$)R$^b$R$^c$, OP(=X$^2$)(O$_p$R$^c$)R$^b$, OP(=X$^2$)(OR$^c$)$_2$, N=CR$^b$R$^c$, NR$^b$N=CR$^b$R$^c$, NR$^b$NR$^b$R$^c$, NR$^b$C(=S)NR$^b$R$^c$, NR$^b$C(=NR$^b$)NR$^b$R$^c$, NR$^b$NR$^b$C(=X$^2$)NR$^b$R$^c$, NR$^b$NR$^b$SO$_2$NR$^b$R$^c$, or N=S(=O)$_p$R$^c$R$^c$ or two geminally bound groups R$^{bb}$ together may form a group selected from =O, =S, =CR$^b$R$^c$, =NR$^c$, =NOR$^c$, and =NNR$^c$R$^c$;

R$^d$ is each independently hydrogen, phenyl, C$_1$-C$_6$-alkyl, C$_2$-C$_6$-alkenyl, C$_2$-C$_6$-alkynyl, C$_3$-C$_8$-cycloalkyl, or C$_1$-C$_6$-alkoxyalkyl, wherein the above mentioned groups may be substituted by one or more halogen;

R$^e$ is each independently C$_1$-C$_4$-alkyl, C$_1$-C$_4$-haloalkyl, C$_1$-C$_4$-alkylcarbonyl, C01-C$_6$ cycloalkyl, or a three- to six-membered saturated, partially unsaturated or aromatic carbo- or heterocyclic ring, which may contain 1 to 3 heteroatoms selected from N(R$^{aa}$)$_p$, O and S, wherein S may be oxidized and wherein the carbo- or heterocyclic ring may be partially or fully substituted by R$^{aa}$;

m is 0, 1, or 2;
p is 0 or 1;
R$^2$ is H, halogen, CN, C$_1$-C$_8$ alkyl, C$_2$-C$_8$ alkenyl, C$_2$-C$_8$ alkynyl, C$_3$-C$_{10}$cycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, or C$_3$-C$_6$ cycloalkenyl, wherein the aforementioned groups may be unsubstituted, partially, or fully substituted with R$^{2a}$, or R$^2$ may form a carbo- or heterocyclic three- to ten-membered ring or a seven- to eleven-membered ring system, which ring or ring system may be saturated, partially unsaturated, or aromatic, and which ring or ring system may contain 1 to 4 heteroatoms selected from N(R$^c$)$_p$, O and S, wherein S may be oxidized, and wherein the carbo- or heterocyclic ring or ring system may be unsubstituted, partially or fully substituted by R$^{2a}$;

with the proviso that if R$^2$ is halogen or CN, then Z is a direct bond;

R$^{2a}$ is each independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, SF$_5$, OCN, SCN, Si(R$^d$)$_3$, C(=N(O)$_p$R$^b$)R$^b$, C(=NNR$^b$R$^c$)R$^b$, C(=NN(C(=O)O$_p$R$^c$)R$^b$)R$^b$, ON=CR$^b$R$^c$, ONR$^b$R$^c$, S(=O)$_o$(=NR$^b$)$_q$R$^c$, SO$_2$NR$^b$(=O)NR$^b$R$^c$, P(=X$^2$)R$^b$R$^c$, OP(=X$^2$)(O$_p$R$^c$)R$^b$, OP(=X$^2$)(OR$^c$)$_2$, N=CR$^b$R$^c$, NR$^b$N=CR$^b$R$^c$, NR$^b$NR$^b$R$^c$, NR$^b$C(=S)NR$^b$R$^c$, NR$^b$C(=NR$^b$)NR$^b$R$^c$, NR$^b$NR$^b$C(=X$^2$)NR$^b$R$^c$, NR$^b$NR$^b$SO$_2$NR$^b$R$^c$, N=S(=O)$_p$R$^c$R$^c$, or a three- to six-membered saturated, or partially unsaturated or aromatic carbo- or heterocyclic ring, which may contain 1 to 3 heteroatoms selected from N(R$^c$)$_p$, O and S, wherein S may be oxidized, and wherein the aforementioned groups and the carbo- or heterocyclic ring may be partially or fully substituted by R$^{2aa}$ or two geminally bound groups R$^{2a}$ together may form a group selected from =O, =S, =CR$^b$R$^c$, =NR$^c$, =NOR$^c$ and =NNR$^c$R$^c$;

R$^{2aa}$ is each independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, SF$_5$, OCN, SCN, Si(R$^d$)$_3$, C(=N(O)$_p$R$^b$)R$^b$, C(=NNR$^b$R$^c$)R$^b$, C(=NN(C(=O)O$_p$R$^c$)R$^b$)R$^b$, ON=CR$^b$R$^c$, ONR$^b$R$^c$, S(=O)$_o$(=NR$^b$)$_q$R$^c$, SO$_2$NR$^b$(=O)NR$^b$R$^c$, P(=X$^2$)R$^b$R$^c$, OP(=X$^2$)(O$_p$R$^c$)R$^b$, OP(=X$^2$)(OR$^c$)$_2$, N=CR$^b$R$^c$, NR$^b$N=CR$^b$R$^c$, NR$^b$NR$^b$R$^c$, NR$^b$C(=S)NR$^b$R$^c$, NR$^b$C(=NR$^b$)NR$^b$R$^c$, NR$^b$NR$^b$C(=X$^2$)NR$^b$R$^c$, NR$^b$NR$^b$SO$_2$NR$^b$R$^c$, or N=S(=O)$_p$R$^c$R$^c$; or two geminally bound groups R$^{2aa}$ together may form a group selected from =O, =S, =CR$^b$R$^c$, =NR$^c$, =NOR$^c$ and =NNR$^c$R$^c$;

X$^2$ is independently O or S;

or an agriculturally or veterinary acceptable salt or tautomer or N-oxide thereof, excluding the compound

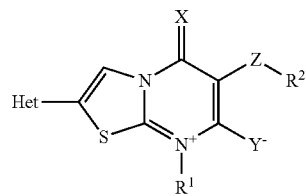

agriculturally and veterinary acceptable salts and tautomers and N-oxides thereof.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes agriculturally and veterinary acceptable salts, tautomers, stereoisomers and N-oxides thereof.

Moreover, the present invention relates to and includes the following embodiments:

- compositions comprising at least one compound of formula (I) as defined above;
- agricultural and veterinary compositions comprising at least one compound of formula (I) as defined above;
- a method for combating or controlling invertebrate pests, infestation or infection by invertebrate pests, which method comprises contacting said pest or its food supply, habitat or breeding grounds with a pesticidally effective amount of at least one compound of formula (I) as defined above or a composition thereof;
- a method for preventing or protecting against invertebrate pests comprising contacting the invertebrate pests, their food supply, habitat or breeding grounds with a compound of formula (I) as defined above or a composition comprising at least one compound of formula (I) as defined above;
- a method for protecting crops, plants, plant propagation material and/or growing plants from attack or infestation by invertebrate pests comprising contacting or treating the crops, plants, plant propagation material and growing plants, or soil, material, surface, space, area or water, in which the crops, plants or plant propagation material is stored or the plant is growing, with a pesticidally effective amount of at least one compound of formula (I) as defined above or a composition comprising at least one compound of formula (I);
- a non-therapeutic method for treating animals infested or infected by parasites or preventing animals from getting infected or infested by parasites or protecting animals from infestation or infection by parasites which comprises orally, topically or parenterally administering or applying to the animals a parasiticidally effective amount of a compound of formula (I) as defined above or a composition comprising at least one compound of formula (I);
- a method for treating or protecting animals against infestation or infection by parasites by administering or applying orally, topically or parenterally to the animals a compound of formula (I) as defined above or a composition comprising at least one compound of formula (I);
- seed comprising a compound of formula (I) as defined above, in an amount of from 0.1 g to 10 kg per 100 kg of seed;
- the use of the compounds of formula (I) as defined above for protecting growing plants or plant propagation material from attack or infestation by invertebrate pests;
- the use of compounds of formula (I) for combating parasites in and on animals;
- a process for the preparation of a veterinary composition for treating, controlling, preventing or protecting animals against infestation or infection by parasites which comprises adding a parasiticidally effective amount of an compound of formula (I) to a carrier composition suitable for veterinary use;
- the use of a compound of formula (I) for the preparation of a medicament for treating, controlling, preventing or protecting animals against infestation or infection by parasites.

The compounds of formula (I) as well as compositions thereof are particularly useful for controlling invertebrate pests, in particular for controlling arthropods and nematodes and especially insects.

The compounds of formula (I) are novel and have not yet been described for pesticidal uses or pesticidal applications in agricultural industry or veterinary practice.

Heterocyclic substituted pyridinium derivatives and their use as pesticides have been disclosed in WO 2009/099929 as well as in WO 2011/017347 and in WO 2011/017351.

However, the particularly substituted pyrimidinium compounds of formula (I) with the characteristic substitution pattern as defined in the present invention have not yet been described.

Depending on the substitution pattern, the compounds of the formula (I) may have one or more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

Depending on the substitution pattern, the compounds of the formula (I) may be present in the form of tautomers. Hence the invention also relates to the tautomers of the formula (I) and the stereoisomers, salts, tautomers and N-oxides of said tautomers.

The compounds of formula (I) may be amorphous or may exist in one or more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective compound I, as well as amorphous or crystalline salts thereof.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of formula (I) which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 8 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl and 2-ethylhexyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 8 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl. Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 8, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 8, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 8 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(=O)" denotes in each case that the group is bound to the remainder of the molecule via a carbonyl C=O group. This is the case e.g. in alkylcarbonyl.

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted by cycloalkyl" an alkyl group which is substituted by a cycloalkyl ring, wherein alkyl and cycloakyl are as herein defined.

The term "cycloalkylalkyl" denotes as well as the term "cycloalkyl which may be substituted by alkyl" a cycloalkyl ring which is substituted by an alkyl group, wherein alkyl and cycloakyl are as herein defined.

The term "alkylcycloalkylalkyl" denotes as well as the term "alkylcycloalkyl which may be substituted by alkyl" an alkylcycloalkyl group which is substituted by an alkyl, wherein alkyl and alkylcycloakyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted by cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1, 1'-bicyclopropyl-2-yl and (1R,2R)-1,1'-bicyclopropyl-2-yl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2, 4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]

azepin-1-, -2-, -3-, -4-, -5-, -6- or -7-yl, 3,4,5,6-tetrahydro [2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

Embodiments and preferred compounds of the present invention for use in pesticidal methods and for insecticidal application purposes are outlined in the following paragraphs.

The remarks made below concerning preferred embodiments of the variables (substituents) of the compounds according to the invention, especially with respect to their substituents X, Y, Z, $X^1$, $X^2$, $Y^1$, A, B, R', R", R''', $R^1$, $R^a$, $R^{aa}$, $R^b$, $R^{bb}$, $R^c$, $R^d$, $R^e$, $R^2$, $R^{2a}$, $R^{2aa}$, m, n, p and Het are valid both on their own and, in particular, in every possible combination with each other and where applicable, the uses, the methods and the compositions according to the invention.

In a particular embodiment, the variables of the compounds of formula (I) have the following meanings, these meanings, both on their own and in combination with one another, being particular embodiments of the compounds of the formula (I):

In one preferred embodiment the compound of formula (I) is a compound of formula (Ia),

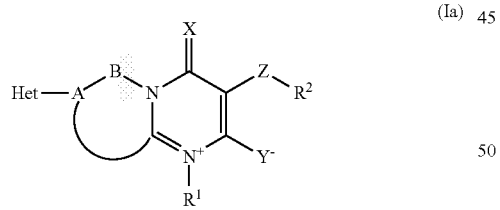
(Ia)

wherein the symbols and indices have the meanings given in formula (I).

In another preferred embodiment A, B and the nitrogen of the pyrimidinium ring together with the contiguous linking carbon atom as depicted in formula (I), and in particular (Ia), form a five or six-membered ring.

In a preferred embodiment, in the compounds of formula (I), B is $CH_2$, N or, if part of a double bond, CH.

More preferred are compounds of formulae (Iaa) and (Iag),

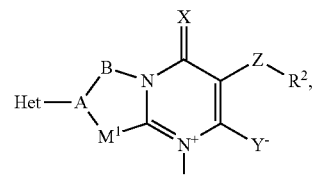
(Iaa)

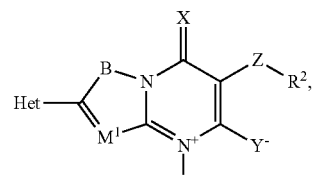
(Iab)

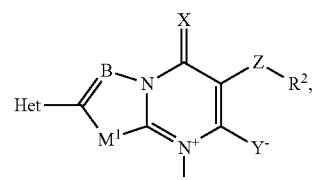
(Iac)

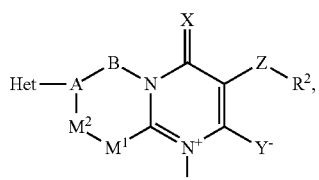
(Iad)

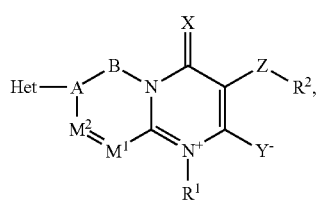
(Iae)

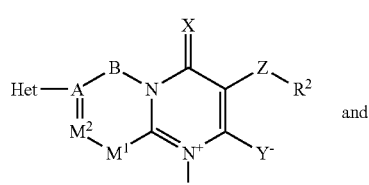
(Iaf)

and

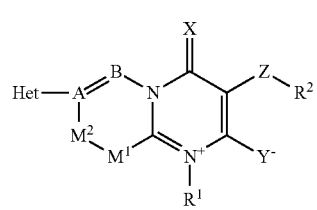
(Iag)

wherein $M^1$, $M^2$ are independently CR'R", $NR^b$, $S(O)_m$, O, or, if part of a double bond, CR' or N.

In one preferred embodiment of the compounds of formula (I) X is O. These compounds correspond to the compounds of formula (I.1).

In a further embodiment of the compounds of the formula (I) X is S. These compounds correspond to the compounds of formula (I.2).

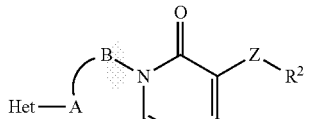
(I.1)

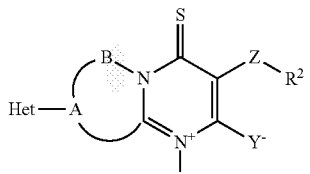
(I.2)

In another embodiment of the compounds of formula (I) Y is S. These compounds correspond to the compounds of formula (I.A).

In another embodiment of the compounds of formula (I), Y is O. These compounds correspond to the compounds of formula (I.B).

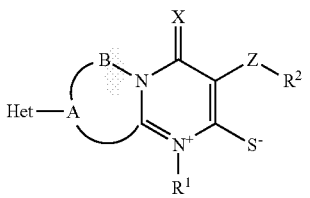
(I.A)

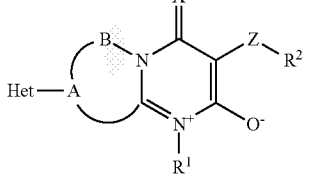
(I.B)

In another embodiment of the compounds of formula (I), Y is S and X is O. These compounds correspond to compounds of formula I.1.A:

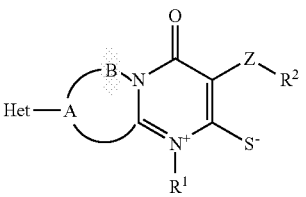
(I.1.A)

In another embodiment of the compounds of formula (I), Y is S and X is S. These compounds correspond to compounds of formula I.2.A.

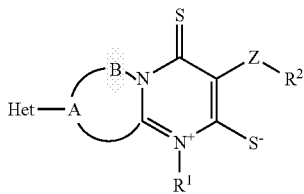
(I.2.A)

In another embodiment of the compounds of formula (I), Y is O and X is O. These compounds correspond to compounds of formula I.1.B.

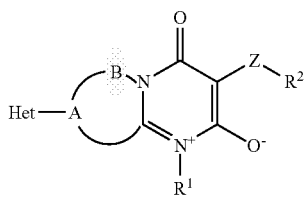
(I.1.B)

In another embodiment of the compounds of formula (I), Y is O and X is S. These compounds correspond to compounds of formula I.2.B.

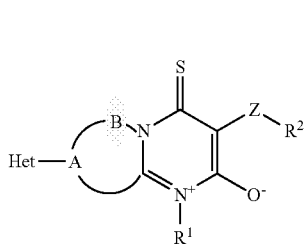
(I.2.B)

Within these embodiments, compounds of formula I.1.B are preferred.

In one embodiment of the compounds of formula (I) Z is a direct bond or $C(R^{aa}R^{aa})O$.

In a further embodiment of the compounds of formula (I) Z is a direct bond.

In an embodiment of the compounds of formula (I) Z is O, $S(O)_m$, $NR^b$, $C(=X^1)$, $C(=X^1)Y^1$, or $Y^1C(=X^1)$. In a further embodiment Z is O, $S(O)_m$, or $NR^b$. In another embodiment, Z is $C(=X^1)$, $C(=X^1)Y^1$, or $Y^1C(=X^1)$.

In an embodiment of the compounds of formula (I) $X^1$ is O.

In an embodiment of the compounds of formula (I) $X^1$ is S.

In an embodiment of the compounds of formula (I) $X^1$ is $NR^b$.

In an embodiment of the compounds of formula (I) $Y^1$ is O.

In an embodiment of the compounds of formula (I) $Y^1$ is S.

In an embodiment of the compounds of formula (I) $Y^1$ is $NR^c$.

In one embodiment of the compounds of formula (I), B is $CH_2$, NH or, if part of a double bond, H or N;

In one embodiment of the compounds of formula (I), $M^1$, $M^2$ are independently $CH_2$, NH, O, or, if part of a double blond, CH or N.

In an embodiment of the compounds of formula (I), A is CH or N, wherein the nitrogen of the pyrimidinium ring taken together with the contiguous linking carbon atom, B and A as depicted in formula (I), form a five or six membered ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH or N, and wherein the nitrogen of the pyrimidinium ring taken together with the contiguous linking carbon atom B and A as depicted in formula (I), form a five membered ring, wherein each remaining ring member is selected from carbon atoms and up to one heteroatoms independently selected from O, S, and $N(R^c)_p$.

In a further embodiment of the compounds of formula (I), A is CH or N, and wherein the nitrogen of the pyrimidinium ring taken together with the contiguous linking carbon atom B and A as depicted in formula (I), form a six membered ring, wherein each remaining ring member is selected from carbon atoms and up to one heteroatom independently selected from O, S, and $N(R^c)_p$.

In a further embodiment, preferred are compounds of formula (Ia), selected from the group of compounds of formulae Ia-1 to Ia-15:

Ia-1
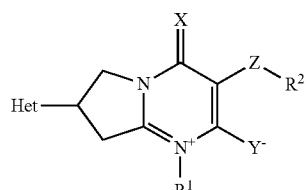

Ia-2
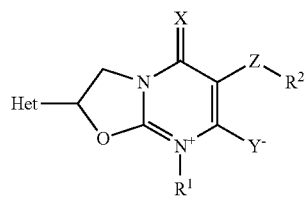

Ia-3
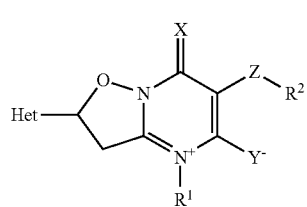

Ia-4
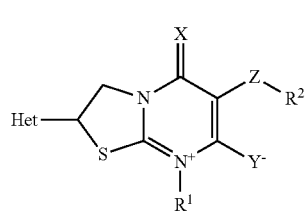

-continued

Ia-5
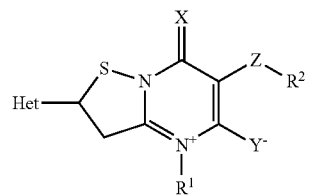

Ia-6
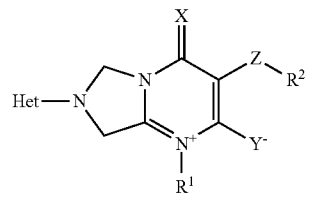

Ia-7
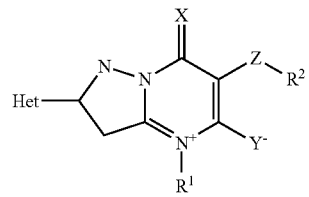

Ia-8
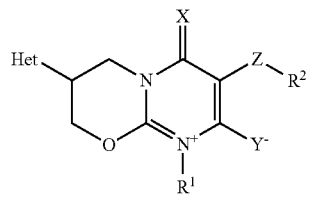

Ia-9
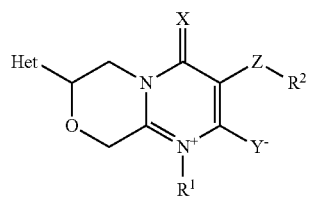

Ia-10
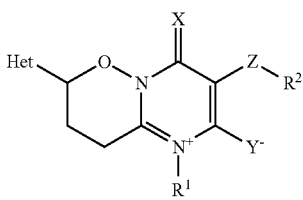

Ia-11
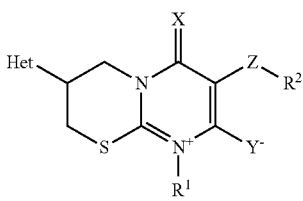

Ia-12
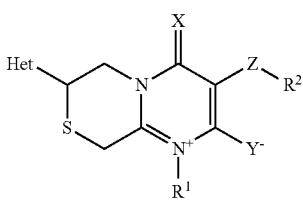

-continued

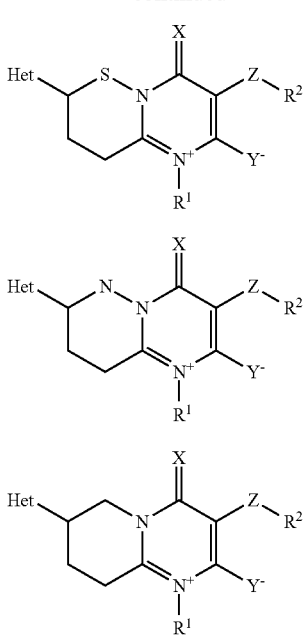

Ia-13

Ia-14

Ia-15

In a further embodiment, compounds of formula (Ia) are selected from the group of compounds of formulae Ia-1, Ia-2, Ia-3, Ia-4, Ia-5, Ia-6, Ia-7 and Ia-15.

In a further embodiment, compounds of formula (I) are selected from the group of compounds of formulae Ia-1, Ia-2, Ia-3, Ia-4, Ia-5, Ia-6 and Ia-7.

In a preferred embodiment, the compounds of formula (I) is a compound of formula Ia-1.

In an other embodiment, the compound of formula (I) is a compound of formula Ia-4.

In an other embodiment, the compound of formula (I) is a compound of formula Ia-5.

In an embodiment, $R^1$ is hydrogen, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_4$-$C_{10}$-cycloalkenyl or $C_5$-$C_{11}$-cycloalkylcycloalkyl, wherein the C-atoms of the aforementioned groups may be unsubstituted, or partially or fully substituted by $R^a$, wherein $R^a$ has the meaning as hereunder described.

In another embodiment, $R^1$ is a three- to ten-membered saturated, or partially saturated or heterocyclic ring system, which may contain 1 to 3 heteroatoms selected from $N(R^c)_p$, O, and S, wherein S may be oxidized and which heterocyclic ring may be unsubstituted or substituted by $R^a$.

In a further embodiment, $R^1$ is hydrogen, $C_1$-$C_4$-alkyl, $C_2$-$C_8$-alkenyl, $C_1$-$C_6$-alkoxy, $C_3$-$C_6$-cycloalkyl or $C_5$-$C_{11}$-cycloalkylcycloalkyl, wherein the C-atoms of the aforementioned groups may be unsubstituted, or partially or fully substituted by halogen.

In a further embodiment $R^1$ is $C_1$-$C_4$-alkyl, $C_2$-$C_8$-alkenyl, $C_3$-$C_6$-cycloalkyl, phenyl or benzyl, wherein the C-atoms of the aforementioned groups may be unsubstituted, or partially or fully substituted by $R^a$, wherein $R^a$ has the meaning as hereunder described, preferably wherein $R^a$ is halogen or $C_1$-$C_4$-alkyl.

In a further embodiment $R^1$ is $C_1$-$C_4$-alkyl, $C_3$-$C_6$-cycloalkyl or phenyl, wherein the C-atoms of the aforementioned groups may be unsubstituted, or partially or fully substituted by halogen or $C_1$-$C_4$-alkyl.

In a further embodiment $R^1$ is $C_1$-$C_4$-alkyl, $C_2$-$C_4$-alkenyl, phenyl or benzyl, wherein the C-atoms of the aforementioned groups may be partially or fully substituted with halogen, preferably Cl or F.

In a further embodiment $R^1$ is $C_1$-$C_4$-alkyl, $C_3$-$C_6$-cycloalkyl or phenyl, preferably $CH_3$, $CH_2CH_3$, $CH(CH_3)_2$, cyclopropyl or phenyl.

In another embodiment $R^1$ is $C_1$-$C_3$-alkyl, preferably $CH_3$, $CH_2CH_3$ or $CH(CH_3)_2$; particularly $R^1$ is $CH_2CH_3$.

In an embodiment, $R^2$ is hydrogen, halogen, CN, $NO_2$, $C_1$-$C_6$-alkyl, $C_1$-$C_6$-haloalkyl, $C_1$-$C_6$-haloalkoxy, $C_1$-$C_6$-alkoxy, $C_2$-$C_6$-alkenyl, $C_2$-$C_6$-alkynyl, $C_3$-$C_6$-cycloalkyl, $C_5$-$C_6$-cycloalkenyl, $C_5$-$C_{14}$-cycloalkylcycloalkyl or $S(O)_m R^b$, wherein the C-atoms of the aforementioned groups may be unsubstituted, or partially or fully substituted by $R^{2a}$.

In an embodiment, $R^2$ is hydrogen, halogen, CN, $C_1$-$C_6$-alkyl, $C_1$-$C_2$-alkoxy-$C_1$-$C_2$-alkyl or $C_3$-$C_6$-cycloalkyl, wherein the C-atoms of the aforementioned groups may be substituted by halogen or CN.

In an embodiment, $R^2$ is hydrogen, halogen, CN or $C_1$-$C_4$-alkyl which may be substituted by halogen.

In a further embodiment $R^2$ is CN.

In a further embodiment, $R^2$ is hydrogen or $C_1$-$C_2$-alkyl, particularly $CH_3$.

In a further embodiment, $R^2$ is $C_1$-$C_6$-haloalkyl, preferably $C_1$-$C_2$-haloalkyl, particularly halomethyl, such as $CF_3$ or $CHF_2$.

In another embodiment, $R^2$ is $C_1$-$C_2$-alkoxy-$C_1$-$C_2$-alkyl, preferably $C_1$-$C_2$-alkoxy-methyl, particularly $CH_2OCH_3$.

In another embodiment, $R^2$ is $C_3$-$C_6$-cycloalkyl, preferably cyclopropyl which may be substituted, preferably by halogen or cyano.

In another embodiment, $R^2$ is $C_2$-$C_6$-alkyl, preferably $C_2$-$C_4$-alkyl, particularly $CH_2CH_3$ or $C(CH_3)_3$.

In another embodiment, $R^2$ is $C_1$-$C_6$-alkyl, preferably $C_1$-$C_2$-alkyl, particularly $CH_3$.

In another embodiment, $R^2$ is halogen, preferably Cl or F, particularly F.

In another embodiment, $R^2$ is a five- or six-membered carbo- or heterocyclic ring, which ring may be unsubstituted, partially, or fully substituted by $R^{2a}$, and wherein $R^{2a}$ is as hereunder defined or $R^{2a}$ is preferably halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by halogen, $C_1$-$C_6$-haloalkyl or $C_1$-$C_6$-haloalkoxy.

In a further embodiment, $R^2$ is a six-membered carbo- or heterocyclic ring, which ring may be unsubstituted, partially, or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by $R^{2aa}$, wherein $R^{2aa}$ is as hereunder defined.

In a further embodiment, $R^2$ is a six-membered aromatic carbocyclic ring, which ring may be unsubstituted, partially, or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by $R^{2aa}$, wherein $R^{2aa}$ is as hereunder defined, preferably $R^{2aa}$ is halogen, $C_1$-$C_6$-haloalkyl or $C_1$-$C_6$-haloalkoxy.

Within this embodiment, $R^2$ is phenyl which may be substituted by halogen, $C_1$-$C_6$-haloalkyl or $C_1$-$C_6$-haloalkoxy. Alternatively, $R^2$ is phenyl which may be substituted by halogen, $C_1$-$C_6$-haloalkyl, $C_1$-$C_6$-alkoxy or $C_1$-$C_6$-haloalkoxy.

Further, within this embodiment $R^2$ is phenyl which may be substituted with phenyl.

Further, within this embodiment $R^2$ is phenyl which may be substituted with phenyl, which may be substituted by halogen, $C_1$-$C_6$-haloalkyl or $C_1$-$C_6$-haloalkoxy In a further embodiment, $R^2$ is a six-membered heterocyclic ring, which contains 1 or 2, preferably 1, heteroatom(s) selected from N—$R^c$, O, and S, wherein S may be oxidised, which heterocyclic ring is unsubstituted or substituted by one or more groups $R^{2a}$, wherein $R^{2a}$ is as hereunder defined.

In an embodiment, $R^a$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms aforementioned which groups may be unsubstituted or substituted by one or more $R^{aa}$, wherein $R^{aa}$ is as hereunder defined.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen.

In an embodiment, $R^a$ is halogen, CN, $NO_2$, $S(O)_mR^b$, $C(O)R^c$, $C(O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted by $R^{aa}$, wherein is as hereunder defined.

In a further embodiment, $R^a$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the afore-mentioned groups may be unsubstituted, partially or fully substituted by $R^{aa}$, wherein $R^{aa}$ is as hereunder defined.

In a further embodiment, $R^a$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted by halogen.

In a further embodiment, $R^a$ is halogen or $C_1$-$C_4$-alkyl. In a further embodiment, $R^a$ is halogen, $C_1$-$C_6$-haloalkyl or $C_1$-$C_6$-alkoxy.

In a further embodiment, $R^a$ is halogen, CN or $C_1$-$C_2$-haloalkyl.

In a further embodiment, $R^a$ is halogen or $C_1$-$C_2$-haloalkyl.

In an embodiment, $R^a$ is halogen, preferably Br, Cl or F, particularly Cl.

In another embodiment, $R^a$ is $C_1$-$C_2$-haloalkyl, preferably halomethyl such as $CHF_2$ or $CF_3$, particularly $CF_3$.

In an embodiment, two geminally bound groups $R^a$ together may form a group selected from =O, =S, =$CR^bR^c$, =$NR^c$, =$NOR^c$ and =$NNR^cR^c$; In another embodiment, two geminally bound groups $R^a$ together may form a group selected from =$CR^bR^c$, =$NR^c$, =$NOR^c$ and =$NNR^cR^c$; In another embodiment, two geminally bound groups $R^a$ together may form a group selected from =O, =S and =$N(C_1$-$C_6$-alkyl).

In another embodiment, two geminally bound groups $R^a$ together may form a =$N(C_1$-$C_6$-alkyl) group.

In an embodiment, $R^b$ is hydrogen, $C_1$-$C_6$-alkyl, $C_1$-$C_6$-haloalkyl, $C_1$-$C_6$-alkoxy, $C_1$-$C_6$-haloalkoxy, phenyl, pyridyl, thiazyl or thienyl, wherein the C-atoms of the afore-mentioned groups may be substituted by $R^{aa}$, wherein $R^{aa}$ is as hereunder defined. In a further embodiment, $R^b$ is hydrogen, $C_1$-$C_6$-alkyl, $C_1$-$C_6$-haloalkyl, $C_1$-$C_6$-alkoxy or $C_1$-$C_6$-haloalkoxy. In a further embodiment, $R^b$ is hydrogen, $C_1$-$C_6$-alkyl or $C_1$-$C_6$-haloalkyl. In an embodiment, $R^b$ is $C_1$-$C_6$-alkyl or $C_1$-$C_6$-haloalkyl. In an embodiment, $R^b$ is H.

In an embodiment, $R^c$ is hydrogen, $C_1$-$C_6$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the C-atoms of the aforementioned groups may be substituted by $R^{aa}$, wherein $R^{aa}$ is as hereunder defined. In a further embodiment, $R^c$ is hydrogen, $C_1$-$C_4$-alkyl, $C_1$-$C_4$-haloalkyl, $C_1$-$C_4$-alkylcarbonyl, or $C_1$-$C_6$-cycloalkyl. In an embodiment, $R^c$ is hydrogen, $C_1$-$C_6$-alkyl or $C_1$-$C_6$-haloalkyl. In an embodiment, $R^c$ is $C_1$-$C_6$-alkyl or $C_1$-$C_6$-haloalkyl. In an embodiment, $R^c$ is H.

In an embodiment, two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted by $R^{bb}$.

In another embodiment, two geminally bound groups $R^bR^b$, $R^cR^b$ or $R^cR^c$ together with the atom to which they are bound, may form a 5- or 6-membered saturated, partially unsaturated or aromatic carbocyclic ring, which ring may be partially or fully substituted by $R^{bb}$, and where in $R^{bb}$ is as hereunder defined.

In another embodiment, two geminally bound groups $R^bR^b$, $R^cR^b$ or $R^cR^c$ together with the atom to which they are bound, may form a 5- or 6-membered saturated, partially unsaturated or aromatic heterocyclic ring, which may contain 1 to 2 heteroatoms or heteroatoms groups selected from N, O, S, NO, SO and $SO_2$, wherein the heterocyclic ring may be partially or fully substituted by $R^{bb}$, and wherein $R^{bb}$ is as hereunder defined.

In an embodiment, $R^d$ is hydrogen, phenyl, $C_1$-$C_4$-alkyl or $C_2$-$C_6$-alkenyl, wherein the afore-mentioned groups may be substituted by one or more halogen. In a further embodiment, $R^d$ is $C_1$-$C_4$-alkyl or phenyl, which may be substituted by halogen. In another embodiment, $R^d$ is $C_1$-$C_4$-alkyl, preferably $CH_3$.

In an embodiment, $R^e$ is $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the aforementioned groups may be substituted by $R^{aa}$, wherein $R^{aa}$ is as hereunder defined. In a further embodiment, $R^e$ is $C_1$-$C_4$-alkyl, $C_1$-$C_4$-haloalkyl, $C_1$-$C_4$-alkylcarbonyl or $C_1$-$C_6$-cycloalkyl. In a further embodiment, $R^e$ is $C_1$-$C_4$-alkyl or $C_1$-$C_4$-haloalkyl.

In an embodiment, $R^{aa}$ is hydrogen, halogen, $C_1$-$C_6$-alkyl or $C_1$-$C_6$-haloalkyl. In another embodiment, $R^{aa}$ is hydrogen, $C_1$-$C_6$-alkoxy or $C_1$-$C_6$-haloalkoxy. In an embodiment, $R^{aa}$ is hydrogen or halogen.

In an embodiment, $R^{2a}$ is halogen, $C_1$-$C_6$-haloalkyl, $C_1$-$C_6$-alkoxy, $C_1$-$C_6$-haloalkoxy, $OR^c$, $C(=O)OR^c$, $C(=O)NR^bR^c$ or phenyl, wherein the C-atoms of the aforementioned groups may be unsubstituted or substituted by one or more $R^{2aa}$, wherein $R^{2aa}$ is as hereunder defined, particularly $R^{2a}$ is halogen, $C_1$-$C_6$-alkoxy, or $C_1$-$C_6$-haloalkoxy.

In an embodiment, two geminally bound groups $R^{2a}$ together may form a group selected from =O, =S and =$N(C_1$-$C_6$-alkyl).

In an embodiment, $R^{2a}$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms of the aforementioned groups may be unsubstituted or substituted by one or more $R^{2aa}$, wherein $R^{2aa}$ is as hereunder defined.

In a further embodiment, $R^{2a}$ is halogen, $C_1$-$C_4$-haloalkyl or $C_3$-$C_6$-haloalkoxy.

In another embodiment, $R^{2a}$ is phenyl which may be substituted by one or more $R^{2aa}$.

In another embodiment, $R^{2a}$ is halogen. In another embodiment, $R^{2a}$ is $C_1$-$C_6$-haloalkyl. In another embodiment, $R^{2a}$ is $C_1$-$C_6$-haloalkoxy.

In another embodiment, $R^{2a}$ is halogen, CN, NO$_2$, S(O)$_m$R$^b$, C(=O)R$^c$, C(=O)OR$^c$, C(O)NR$^b$R$^c$, C(=S)NR$^b$R$^c$, C$_1$-C$_6$-alkyl, C$_3$-C$_6$-cycloalkyl, C$_2$-C$_6$-alkenyl, C$_2$-C$_6$-alkynyl, C$_1$-C$_6$-alkoxy, C$_2$-C$_6$-alkenyloxy or C$_2$-C$_6$-alkynyloxy, which C-atoms of the aforementioned groups may be unsubstituted, partially or fully substituted by R$^{aa}$, wherein is as hereunder defined.

In further embodiment, $R^{2a}$ is, C(=O)OR$^c$ or C(=O)NR$^b$R$^c$.

In another embodiment, $R^{2a}$ is halogen, CN, C$_1$-C$_6$-alkyl, C$_3$-C$_6$-cycloalkyl, C$_2$-C$_6$-alkenyl, C$_2$-C$_6$-alkynyl, C$_1$-C$_6$-alkoxy, C$_2$-C$_6$-alkenyloxy or C$_2$-C$_6$-alkynyloxy, which C-atoms of the afore-mentioned groups may be unsubstituted, partially or fully substituted by R$^{2aa}$, wherein R$^{2aa}$ is as hereunder defined.

In an embodiment, $R^{2a}$ is Br, Cl or F, particularly Cl.

In another embodiment, $R^{2a}$ is C$_1$-C$_2$-haloalkyl, preferably halomethyl such as CHF$_2$ or CF$_3$, particularly CF$_3$.

In an embodiment, $R^{2aa}$ is halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), or S(=O)$_p$(=N(C$_1$-C$_6$-alkyl))(C$_1$-C$_6$-alkyl) or two geminally bound groups R$^{2aa}$ together may form a group selected from =O, =S and =N(C$_1$-C$_6$-alkyl).

In an embodiment, $R^{2aa}$ is halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), or S(=O)$_p$(=N(C$_1$-C$_6$-alkyl))(C$_1$-C$_6$-alkyl). In another embodiment, two geminally bound groups R$^{2aa}$ together may form a group selected from =O, =S and =N(C$_1$-C$_6$-alkyl).

In an embodiment, $R^{bb}$ is halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), S(=O)$_p$(=N(C$_1$-C$_6$-alkyl))(C$_1$-C$_6$-alkyl), or two geminally bound groups R$^{bb}$ together may form a group selected from =O, =S and =N(C$_1$-C$_6$-alkyl).

In an embodiment R' and R", each independently, are H, halogen or C$_1$-C$_4$-alkyl.

In an embodiment, m is 0. In another embodiment, m is 1. In another embodiment, m is 2. In an embodiment, p is 0. In another embodiment, p is 1.

In an embodiment Het is a five- or six-membered saturated, partially unsaturated or aromatic heterocyclic ring, which may contain 1 to 4 heteroatoms selected from N(R$^c$)$_p$, O and S, wherein the heterocyclic ring is substituted by (R$^a$)$_n$ and the remaining variables in the meaning of Het are as above defined.

In an embodiment Het is a five- or six-membered saturated, partially unsaturated or aromatic heterocyclic ring, which may contain 1 or 2 heteroatoms selected from N(R$^c$)$_p$, O and S, wherein the heterocyclic ring is substituted by (R$^a$)$_n$.

In an embodiment Het is a five-membered aromatic heterocyclic ring, which contains 2 heteroatoms selected from N(R$^c$)$_p$, O and S, wherein the heterocyclic ring is substituted by (R$^a$)$_n$.

In an embodiment Het is a five-membered saturated heterocyclic ring, which contains 1 heteroatom selected from N(R$^c$)$_p$, O and S, preferably O, wherein the heterocyclic ring is substituted by (R$^a$)$_n$.

In an embodiment Het is a six-membered aromatic heterocyclic ring, which contains 2 heteroatoms selected from N(R$^c$)$_p$, O and S, preferably N(R$^c$)$_p$, wherein the heterocyclic ring is substituted by (R$^a$)$_n$.

In an embodiment Het is a six-membered aromatic heterocyclic ring, which contains 1 heteroatom selected from N(R$^c$)$_p$, O and S, preferably N(R$^c$)$_p$, wherein the heterocyclic ring is substituted by (R$^a$)$_n$.

In an embodiment Het is pyridyl which is substituted by (R$^a$)$_n$.

In an embodiment Het is tetrahydrofuryl which is substituted by (R$^a$)$_n$.

In all the above embodiments defining Het, n is 0, 1, 2, 3, 4 or 5 (as far as possible for a given ring-size), preferably 0, 1 or 2, more preferably 0 or 1.

In another embodiment, Het is selected from any one of the following ring systems D-1 to D-56:

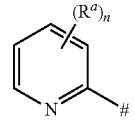

D-1

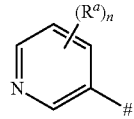

D-2

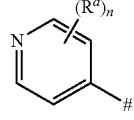

D-3

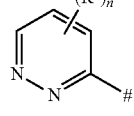

D-4

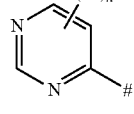

D-5

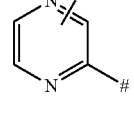

D-6

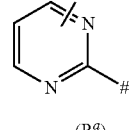

D-7

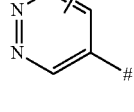

D-8

-continued
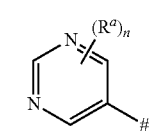 D-9
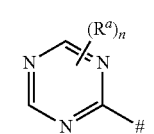 D-10
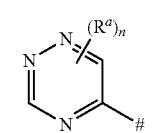 D-11
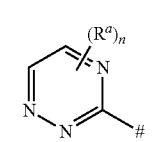 D-12
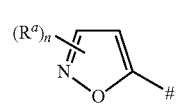 D-13
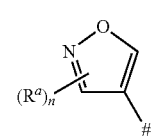 D-14
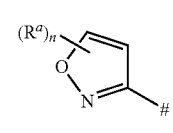 D-15
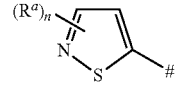 D-16
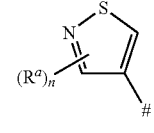 D-17
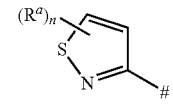 D-18
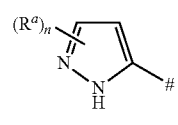 D-19
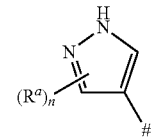 D-20
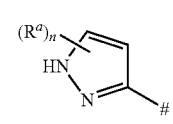 D-21
-continued
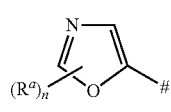 D-22
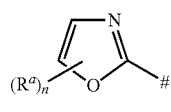 D-23
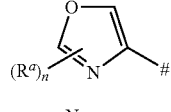 D-24
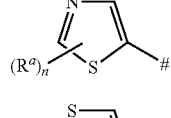 D-25
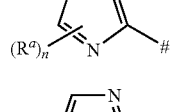 D-26
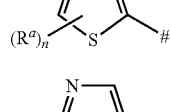 D-27
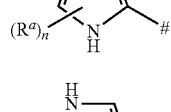 D-28
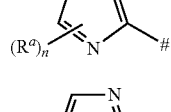 D-29
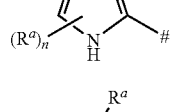 D-30
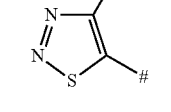 D-31
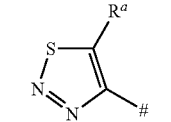 D-32
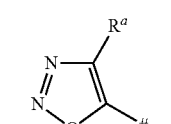 D-33
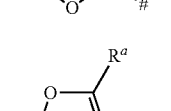 D-34
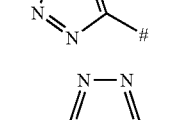 D-35

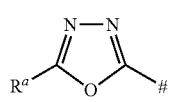 D-36
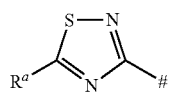 D-37
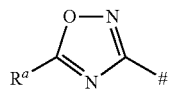 D-38
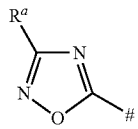 D-39
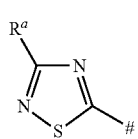 D-40
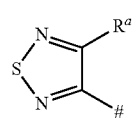 D-41
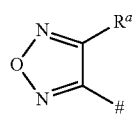 D-42
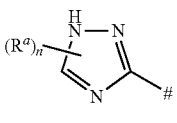 D-43
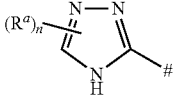 D-44
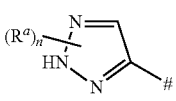 D-45
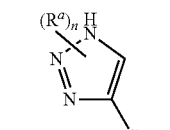 D-46
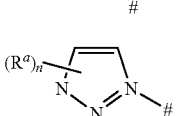 D-47
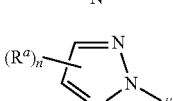 D-48
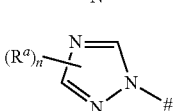 D-49
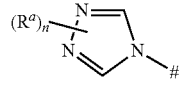 D-50
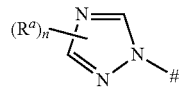 D-51
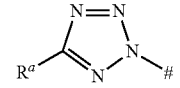 D-52
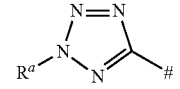 D-53
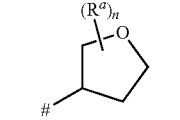 D-54
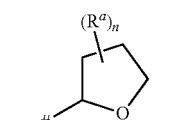 D-55
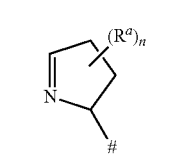 D-56
Wherever used in a structure, the following: # denotes the bond to A in formula (I) In a further embodiment Het is selected from any one of the following ring systems:
D-1
D-2
D-3
D-5

-continued
D-6 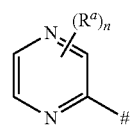
D-7 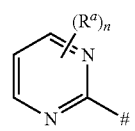
D-16 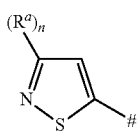
D-17 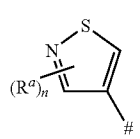
D-20 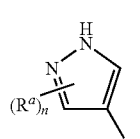
D-22 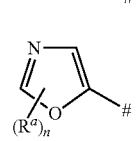
D-23 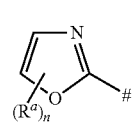
D-24 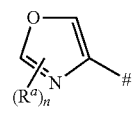
D-25 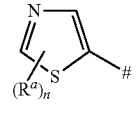
D-26 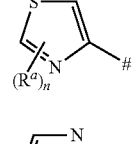
D-27 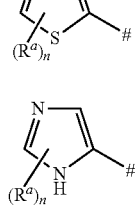
D-28 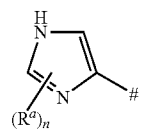
-continued
D-29 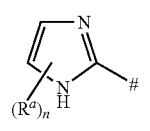
D-30 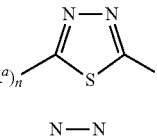
D-35 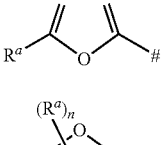
D-36 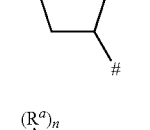
D-54 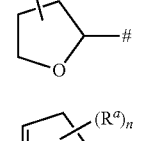
D-55 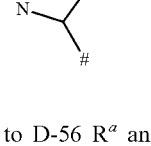
D-56 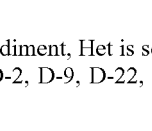
In formulae D-1 to D-56 $R^a$ and n have the meanings given above.
In a further embodiment, Het is selected from the following rings systems D-2, D-9, D-22, D25, D-28, D-29, D-54 and D-56:
D-2 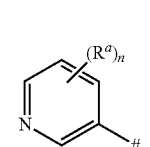
D-9 
D-22 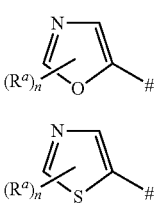
D-25

D-28
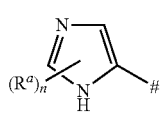

D-29
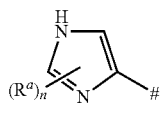

D-54
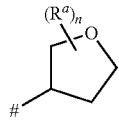

D-56
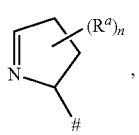

wherein $R^a$ is halogen, $C_1$-$C_4$-haloalkyl, $C_1C4$-alkoxy or $C_1$-$C_4$-alkylthio or phenyl; preferably $R^a$ is halogen or halomethyl, preferably wherein n is 0 or 1.

In a further embodiment, Het is selected from the following rings systems D-2, D-9, D-25 and D-56:

D-2
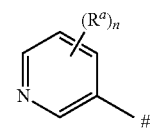

D-9
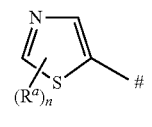

D-25
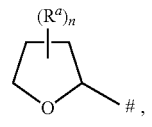

D-56
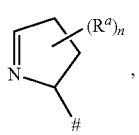

wherein $R^a$ is halogen, $C_1$-$C_4$-haloalkyl, $C_1C4$-alkoxy or $C_1$-$C_4$-alkylthio or phenyl, preferably halogen or $C_1$-$C_4$-haloalkyl; more preferably $R^a$ is Cl, Br, F or $CF_3$, most preferably $R^a$ is Cl or $CF_3$ and preferably wherein n is 0, 1 or 2. In a further embodiment, the invention relates to compounds of formula (I), wherein X, Y are each O;

A is CH and the nitrogen of the pyrimidinium ring taken together with the contiguous linking carbon atom and A as depicted in formula (I), form a five or six membered ring, wherein each remaining ring member is selected from 2 and 3 carbon atoms;

$R^1$ is $CH_3$, $CH_2CH_3$, isopropyl, cyclopropyl, $CH_2CF_3$, phenyl, allyl or benzyl;

B is $CH_2$, NH or, if part of a double bond, CH or N;

$R^2$ is phenyl which may be substituted by halogen, $C_1$-$C_6$-haloalkyl, $C_1$-$C_6$-haloalkoxy or phenyl;

Z is a direct bond and

Het is D-2, D-9, D-25 or D-56 and $R^a$ is Cl, Br, F, $SCH_3$, $CF_3$, $OCH_3$ or phenyl.

In a further embodiment Het is selected from the following rings systems D-2, D-25 or D-54:

D-2
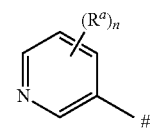

D-25
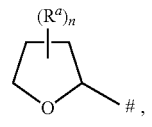

D-54
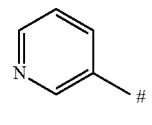

wherein $R^a$ is halogen or $C_1$-$C_4$-haloalkyl; preferably $R^a$ is Cl, Br, F or $CF_3$, most preferably $R^a$ is Cl or $CF_3$, and preferably wherein n is 0 or 1.

In another embodiment Het is selected from the following rings systems D-2a, D-2b, D-2c, D25a and D-54a:

D-2a
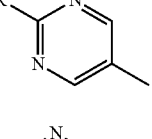

D-9a
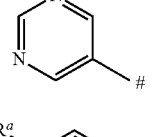

D-9b
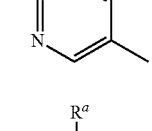

D-2b
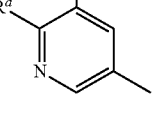

D-2c
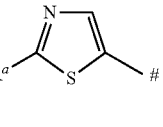

D-25a

-continued

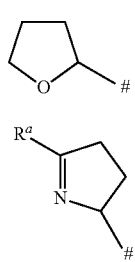

D-54a

D-56 wherein $R^a$ are independently from each other selected from Cl, Br, F and $CF_3$.

In another embodiment Het is D-2, preferably D-2b or D-2c, particularly D-2b, wherein $R^a$ is Cl or $CF_3$.

In a further embodiment Het is D-2a.

In another embodiment, Het is D-25, preferably D-25a substituted by Cl.

In another embodiment, Het is D-9, preferably D-9a or D9b.

In another embodiment, Het is D-56, preferably D-56a.

In another embodiment, Het is D-2-1

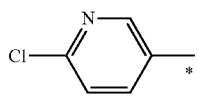

D-2-1

In another embodiment, Het is D-25-1:

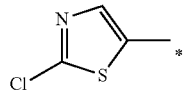

D-25-1

In one embodiment, the compounds of the formula I are compounds of the formula I-ex

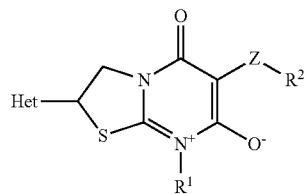

I-ex in which $R^1$ is $C_1$-$C_4$-alkyl; Het is D-2-1, Z is a direct bond, and $R^2$ is phenyl, which may be substituted by halogen, $C_1$-$C_6$-haloalkyl, $C_1$-$C_6$-alkoxy, $C_1$-$C_6$-alkoxy-$C_1$-$C_6$-alkyloxy or $R^2$ is phenyl which may be further substituted by halogen, $C_1$-$C_6$-haloalkyl, $C_1$-$C_6$-alkoxy, or $R^2$ is benzyl which may be further substituted by halogen, $C_1$-$C_6$-haloalkyl, $C_1$-$C_6$-alkoxy, or $R^2$ is thienyl.

In this embodiment, $R^2$ is preferably phenyl, which may be substituted by halogen, $C_1$-$C_6$-haloalkyl, $C_1$-$C_6$-alkoxy, $C_1$-$C_6$-alkoxy-$C_1$-$C_6$-alkyloxy or phenyl which may be further substituted by halogen, $C_1$-$C_6$-haloalkyl, $C_1$-$C_6$-alkoxy.

In one embodiment, the compounds of the formula I are compounds of the formula I-ex in which $R^1$ is $C_1$-$C_4$-alkyl; Het is D-25-1, Z is a direct bond, and $R^2$ is phenyl, which may be substituted by halogen, $C_1$-$C_6$-haloalkyl, $C_1$-$C_6$-alkoxy, $C_1$-$C_6$-alkoxy-$C_1$-$C_6$-alkyloxy or $R^2$ is phenyl which may be further substituted by halogen, $C_1$-$C_6$-haloalkyl, $C_1$-$C_6$-alkoxy, or $R^2$ is benzyl which may be further substituted by halogen, $C_1$-$C_6$-haloalkyl, $C_1$-$C_6$-alkoxy, or $R^2$ is thienyl.

In this embodiment, $R^2$ is preferably phenyl, which may be substituted by halogen, $C_1$-$C_6$-haloalkyl, $C_1$-$C_6$-alkoxy, $C_1$-$C_6$-alkoxy-$C_1$-$C_6$-alkyloxy or phenyl which may be further substituted by halogen, $C_1$-$C_6$-haloalkyl, $C_1$-$C_6$-alkoxy.

In particular, with a view to their use, preference is given to the compounds of the formula (I) compiled in the tables below, which compounds correspond to the compounds of formulae I.1.B (i.e. wherein X and Y are O) and to the preferred compounds of formula Ia-1, Ia-2, Ia-3, Ia-4, Ia-5, Ia-6, Ia-7, and Ia-15. Each of the groups mentioned for the substituents in the tables are furthermore per se, independently of the combination in which they are mentioned, a particularly preferred aspect of the substituent in question. Further, each individual meaning of a substituent in the tables constitutes a particularly preferred embodiment of the substituents in question.

Table 1: Compounds of the formula (III-1) corresponding to the compounds of the formula Ia-1, in which X and Y are O, Het is D-2b wherein $R^a$ is Cl, and the combination of $R^1$, $ZR^2$ for a compound corresponds in each case to one line of Table A:

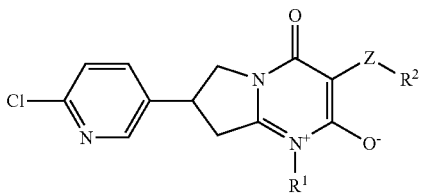

III-1

Table 2: Compounds of the formula (III-2) corresponding to the compounds of the formula Ia-2, in which X and Y are O, Het is D-2b wherein $R^a$ is Cl, and the combination of $R^1$, $ZR^2$ for a compound corresponds in each case to one line of Table A:

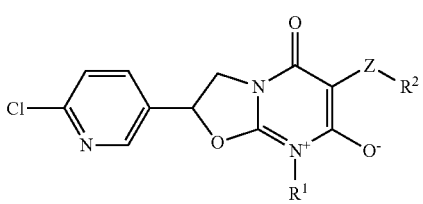

III-2

Table 3: Compounds of the formula (III-3) corresponding to the compounds of the formula Ia-3, in which X and Y are O, Het is D-2b wherein $R^a$ is Cl, and the combination of $R^1$, $ZR^2$ for a compound corresponds in each case to one line of Table A.

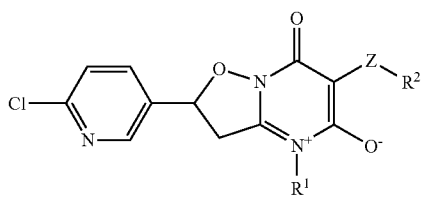

III-3

Table 4: Compounds of the formula (III-4) corresponding to the compounds of the formula Ia-4, in which X and Y are O, Het is D-2b wherein $R^a$ is Cl, and the combination of $R^1$, $ZR^2$ for a compound corresponds in each case to one line of Table A.

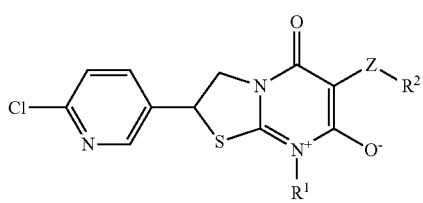

III-4

Table 5: Compounds of the formula (III-5) corresponding to the compounds of the formula Ia-5, in which X and Y are O, Het is D-2b wherein $R^a$ is Cl, and the combination of $R^1$, $ZR^2$ for a compound corresponds in each case to one line of Table A.

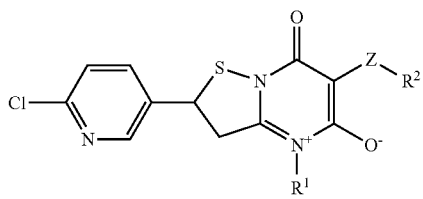

III-5

Table 6: Compounds of the formula (III-6) corresponding to the compounds of the formula Ia-6, in which X and Y are O, Het is D-2b wherein $R^a$ is Cl, and the combination of $R^1$, $ZR^2$ for a compound corresponds in each case to one line of Table A.

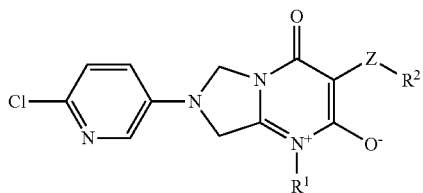

III-6

Table 7 Compounds of the formula (III-7) corresponding to the compounds of the formula Ia-7, in which X and Y are O, Het is D-2b wherein $R^a$ is Cl, and the combination of $R^1$, $ZR^2$ for a compound corresponds in each case to one line of Table A.

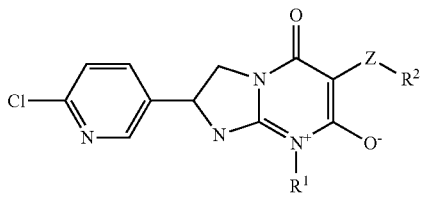

III-7

Table 8: Compounds of the formula (III-8) corresponding to the compounds of the formula Ia-15, in which X and Y are O, Het is D-2b wherein $R^a$ is Cl, and the combination of $R^1$, $ZR^2$ for a compound corresponds in each case to one line of Table A.

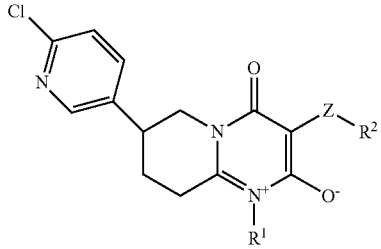

III-8

Table 9: Compounds of the formula (III-9) corresponding to the compounds of the formula Ia-1, in which X and Y are O, Het is D-25a wherein $R^a$ is Cl, and the combination of $R^1$, $ZR^2$ for a compound corresponds in each case to one line of Table A:

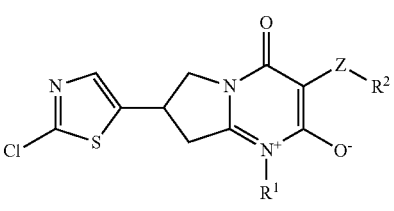

III-9

Table 10: Compounds of the formula (III-10) corresponding to the compounds of the formula Ia-2, in which X and Y are O, Het is D-25a wherein $R^a$ is Cl, and the combination of $R^1$, $ZR^2$ for a compound corresponds in each case to one line of Table A.

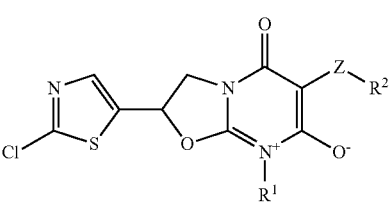

III-10

Table 11: Compounds of the formula (III-11) corresponding to the compounds of the formula Ia-3, in which X and Y are O, Het is D-25a wherein $R^a$ is Cl, and the combination of $R^1$, $ZR^2$ for a compound corresponds in each case to one line of Table A.

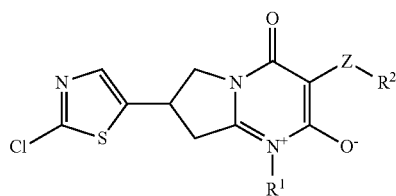

III-11

Table 12: Compounds of the formula (III-12) corresponding to the compounds of the formula Ia-4, in which X and Y are O, Het is D-25a wherein $R^a$ is Cl, and the combination of $R^1$, $ZR^2$ for a compound corresponds in each case to one line of Table A.

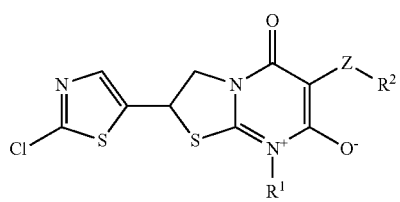

III-12

Table 13: Compounds of the formula (III-13) corresponding to the compounds of the formula Ia-5, in which X and Y are O, Het is D-25a wherein $R^a$ is Cl, and the combination of $R^1$, $ZR^2$ for a compound corresponds in each case to one line of Table A.

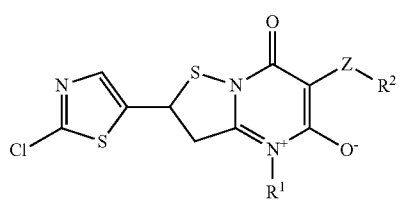

III-13

Table 14: Compounds of the formula (III-14) corresponding to the compounds of the formula Ia-6, in which X and Y are O, Het is D-25a wherein $R^a$ is Cl, and the combination of $R^1$, $ZR^2$ for a compound corresponds in each case to one line of Table A.

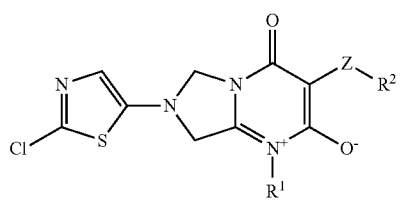

III-14

Table 15 Compounds of the formula (III-15) corresponding to the compounds of the formula Ia-7, in which X and Y are O, Het is D-25a wherein $R^a$ is Cl, and the combination of $R^1$, $ZR^2$ for a compound corresponds in each case to one line of Table A.

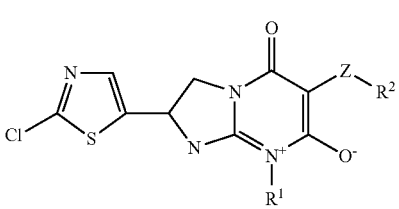

III-15

Table 16: Compounds of the formula (III-16) corresponding to the compounds of the formula Ia-15, in which X and Y are O, Het is D-25a wherein $R^a$ is Cl, and the combination of $R^1$, $ZR^2$ for a compound corresponds in each case to one line of Table A.

III-16

Table 17: Compounds of the formula (III-17) corresponding to the compounds of the formula Ia-1, in which X and Y are O, Het is D-2b wherein $R^a$ is Cl, and the combination of $R^1$, $ZR^2$ for a compound corresponds in each case to one line of Table A:

III-17

Table 18: Compounds of the formula (III-18) corresponding to the compounds of the formula Ia-2, in which X and Y are O, Het is D-9b, and the combination of $R^1$, $ZR^2$ for a compound corresponds in each case to one line of Table A:

III-18

Table 19: Compounds of the formula (III-19) corresponding to the compounds of the formula Ia-3, in which X and Y are O, Het is D-9b, and the combination of $R^1$, $ZR^2$ for a compound corresponds in each case to one line of Table A.

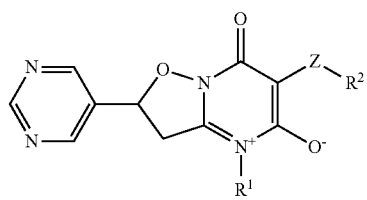

III-19

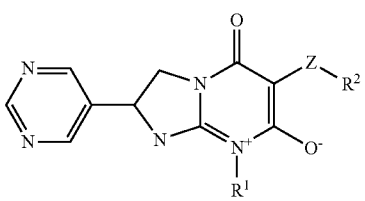

III-23

Table 20: Compounds of the formula (III-20) corresponding to the compounds of the formula Ia-4, in which X and Y are O, Het is D-9b, and the combination of R¹, ZR² for a compound corresponds in each case to one line of Table A.

Table 24: Compounds of the formula (III-24) corresponding to the compounds of the formula Ia-15, in which X and Y are O, Het is D-9b, and the combination of R¹, ZR² for a compound corresponds in each case to one line of Table A.

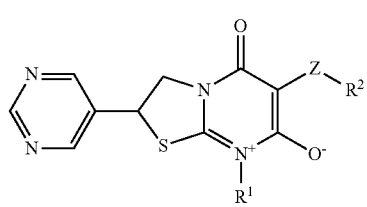

III-20

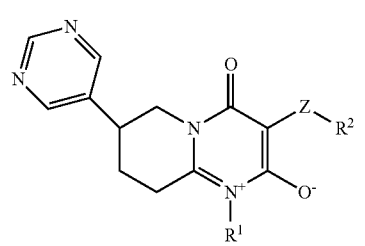

III-24

Table 21: Compounds of the formula (III-21) corresponding to the compounds of the formula Ia-5, in which X and Y are O, Het is D-9b, and the combination of R¹, ZR² for a compound corresponds in each case to one line of Table A.

Table 25: Compounds of the formula (III-25) corresponding to the compounds of the formula Ia-1, in which X and Y are O, Het is D-25a wherein $R^a$ is S—CH₃, and the combination of R¹, ZR² for a compound corresponds in each case to one line of Table A:

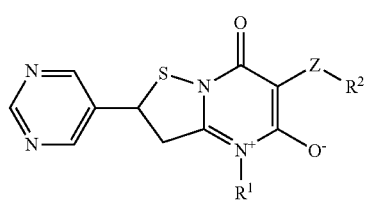

III-21

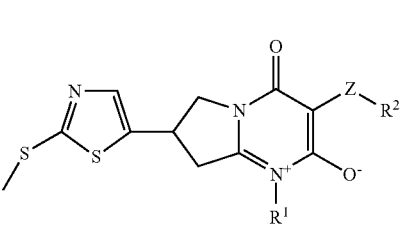

III-25

Table 22: Compounds of the formula (III-22) corresponding to the compounds of the formula Ia-6, in which X and Y are O, Het is D-9b, and the combination of R¹, ZR² for a compound corresponds in each case to one line of Table A.

Table 26: Compounds of the formula (III-26) corresponding to the compounds of the formula Ia-2, in which X and Y are O, Het is D-25a wherein $R^a$ is S—CH₃, and the combination of R¹, ZR² for a compound corresponds in each case to one line of Table A.

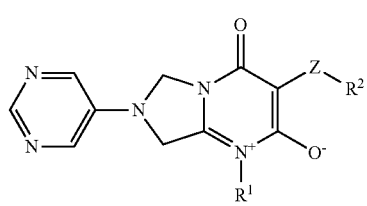

III-22

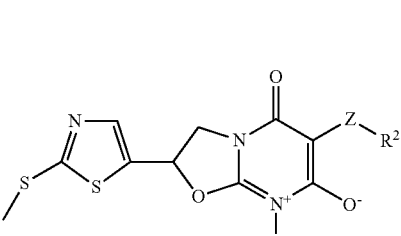

III-26

Table 23 Compounds of the formula (III-23) corresponding to the compounds of the formula Ia-7, in which X and Y are O, Het is D-9b, and the combination of R¹, ZR² for a compound corresponds in each case to one line of Table A.

Table 27: Compounds of the formula (III-27) corresponding to the compounds of the formula Ia-3, in which X and Y are O, Het is D-25a wherein $R^a$ is S—CH₃, and the combination of R¹, ZR² for a compound corresponds in each case to one line of Table A.

Table 28: Compounds of the formula (III-28) corresponding to the compounds of the formula Ia-4, in which X and Y are O, Het is D-25a wherein $R^a$ is S—CH$_3$, and the combination of $R^1$, $ZR^2$ for a compound corresponds in each case to one line of Table A.

Table 29: Compounds of the formula (III-29) corresponding to the compounds of the formula Ia-5, in which X and Y are O, Het is D-25a wherein $R^a$ is S—CH$_3$, and the combination of $R^1$, $ZR^2$ for a compound corresponds in each case to one line of Table A.

Table 30: Compounds of the formula (III-30) corresponding to the compounds of the formula Ia-6, in which X and Y are O, Het is D-25a wherein $R^a$ is S—CH$_3$, and the combination of $R^1$, $ZR^2$ for a compound corresponds in each case to one line of Table A.

Table 31 Compounds of the formula (III-31) corresponding to the compounds of the formula Ia-7, in which X and Y are O, Het is D-25a wherein $R^a$ is S—CH$_3$, and the combination of $R^1$, $ZR^2$ for a compound corresponds in each case to one line of Table A.

Table 32: Compounds of the formula (III-32) corresponding to the compounds of the formula Ia-15, in which X and Y are O, Het is D-25a wherein $R^a$ is S—CH$_3$, and the combination of $R^1$, $ZR^2$ for a compound corresponds in each case to one line of Table A.

Table 33: Compounds of the formula (III-33) corresponding to the compounds of the formula Ia-1, in which X and Y are O, Het is D-2c wherein $R^a$ is Cl and Phenyl, and the combination of $R^1$, $ZR^2$ for a compound corresponds in each case to one line of Table A:

Table 34: Compounds of the formula (III-34) corresponding to the compounds of the formula Ia-2, in which X and Y are O, Het is D-2c wherein $R^a$ is Cl and Phenyl, and the combination of $R^1$, $ZR^2$ for a compound corresponds in each case to one line of Table A:

Table 35: Compounds of the formula (III-35) corresponding to the compounds of the formula Ia-3, in which X and Y are O, Het is D-2c wherein $R^a$ is Cl and phenyl, and the combination of $R^1$, $ZR^2$ for a compound corresponds in each case to one line of Table A.

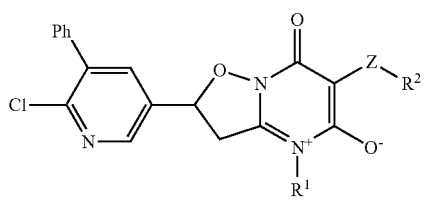

III-35

Table 36: Compounds of the formula (III-36) corresponding to the compounds of the formula Ia-4, in which X and Y are O, Het is D-2c wherein $R^a$ is Cl and phenyl, and the combination of $R^1$, $ZR^2$ for a compound corresponds in each case to one line of Table A.

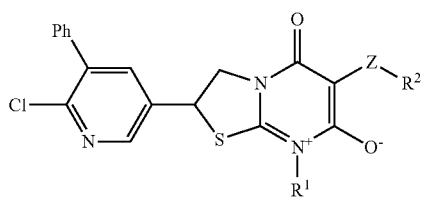

III-36

Table 37: Compounds of the formula (III-37) corresponding to the compounds of the formula Ia-5, in which X and Y are O, Het is D-2c wherein $R^a$ is Cl and phenyl, and the combination of $R^1$, $ZR^2$ for a compound corresponds in each case to one line of Table A.

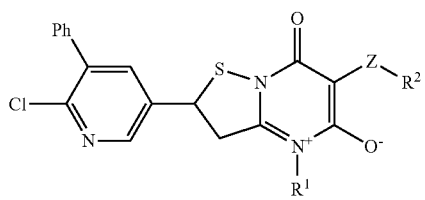

III-37

Table 38: Compounds of the formula (III-38) corresponding to the compounds of the formula Ia-6, in which X and Y are O, Het is D-2c wherein $R^a$ is Cl and phenyl, and the combination of $R^1$, $ZR^2$ for a compound corresponds in each case to one line of Table A.

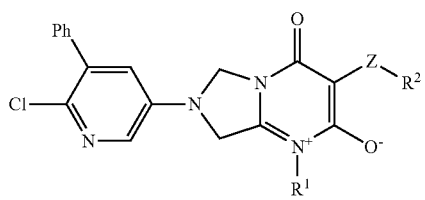

III-38

Table 39 Compounds of the formula (III-39) corresponding to the compounds of the formula Ia-7, in which X and Y are O, Het is D-2c wherein $R^a$ is Cl and phenyl, and the combination of $R^1$, $ZR^2$ for a compound corresponds in each case to one line of Table A.

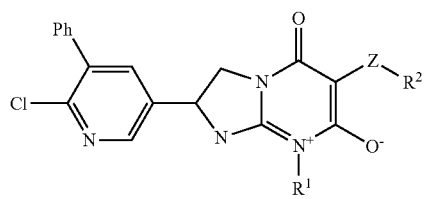

III-39

Table 40: Compounds of the formula (III-40) corresponding to the compounds of the formula Ia-15, in which X and Y are O, Het is D-2c wherein $R^a$ is Cl and phenyl, and the combination of $R^1$, $ZR^2$ for a compound corresponds in each case to one line of Table A.

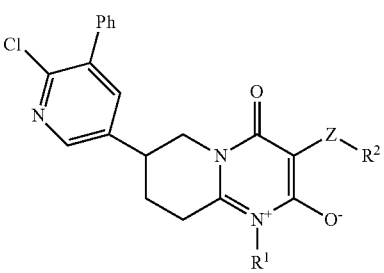

III-40

Table 41: Compounds of the formula (III-41) corresponding to the compounds of the formula Ia-1, in which X and Y are O, Het is D-56a wherein $R^a$ is O-Me, and the combination of $R^1$, $ZR^2$ for a compound corresponds in each case to one line of Table A:

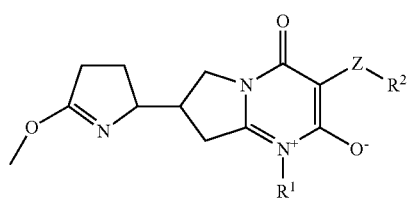

III-41

Table 42: Compounds of the formula (III-42) corresponding to the compounds of the formula Ia-2, in which X and Y are O, Het is D-56a wherein $R^a$ is O-Me, and the combination of $R^1$, $ZR^2$ for a compound corresponds in each case to one line of Table A.

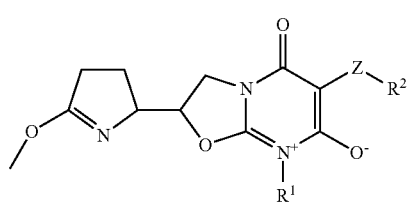

III-42

Table 43: Compounds of the formula (III-43) corresponding to the compounds of the formula Ia-3, in which X and Y are O, Het is D-56a wherein $R^a$ is O-Me, and the combination of $R^1$, $ZR^2$ for a compound corresponds in each case to one line of Table A.

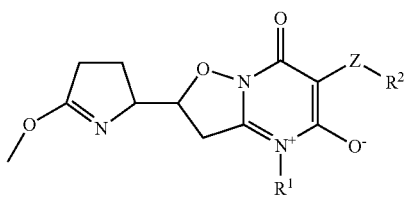

III-43

Table 44: Compounds of the formula (III-12) corresponding to the compounds of the formula Ia-4, in which X and Y are O, Het is D-56a wherein $R^a$ is O-Me, and the combination of $R^1$, $ZR^2$ for a compound corresponds in each case to one line of Table A.

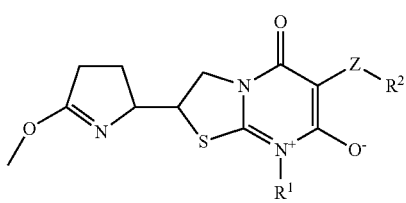

III-44

Table 45: Compounds of the formula (III-45) corresponding to the compounds of the formula Ia-5, in which X and Y are O, Het is D-56a wherein $R^a$ is O-Me, and the combination of $R^1$, $ZR^2$ for a compound corresponds in each case to one line of Table A.

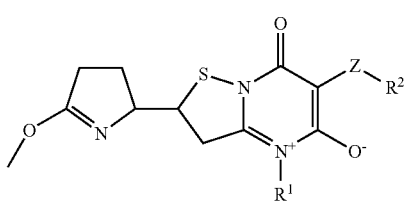

III-45

Table 46: Compounds of the formula (III-46) corresponding to the compounds of the formula Ia-6, in which X and Y are O, Het is D-56a wherein $R^a$ is O-Me, and the combination of $R^1$, $ZR^2$ for a compound corresponds in each case to one line of Table A.

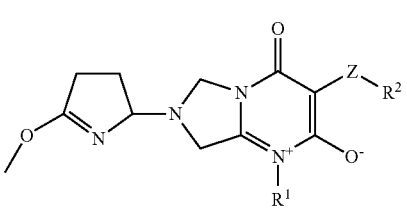

III-46

Table 47: Compounds of the formula (III-47) corresponding to the compounds of the formula Ia-7, in which X and Y are O, Het is D-56a wherein $R^a$ is O-Me, and the combination of $R^1$, $ZR^2$ for a compound corresponds in each case to one line of Table A.

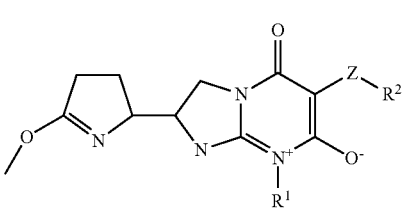

III-47

Table 48: Compounds of the formula (III-48) corresponding to the compounds of the formula Ia-15, in which X and Y are O, Het is D-56a wherein $R^a$ is O-Me, and the combination of $R^1$, $ZR^2$ for a compound corresponds in each case to one line of Table A.

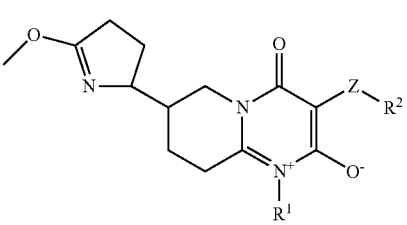

III-48

TABLE A

| No. | $ZR^2$ | $R^1$ |
|---|---|---|
| A-1 | $C_6H_5$ | $CH_3$ |
| A-2 | 2-fluorophenyl | $CH_3$ |
| A-3 | 2-methoxyphenyl | $CH_3$ |
| A-4 | 2,4-difluorophenyl | $CH_3$ |
| A-5 | 2,6-difluorophenyl | $CH_3$ |
| A-6 | 4-fluorophenyl | $CH_3$ |
| A-7 | $CO_2CH_2CH_3$ | $CH_3$ |
| A-8 | $C(O)CF_3$ | $CH_3$ |
| A-9 | $C(O)C_6H_5$ | $CH_3$ |
| A-10 | 3-methoxyphenyl | $CH_3$ |
| A-11 | 3-cyanophenyl | $CH_3$ |
| A-12 | 3-($CO_2CH_2CH_3$)phenyl | $CH_3$ |
| A-13 | 3-($C(O)N(CH_3)_2$)phenyl | $CH_3$ |
| A-14 | 3-(trifluoromethyl)phenyl | $CH_3$ |
| A-15 | 3-(trifluoromethoxy)phenyl | $CH_3$ |
| A-16 | 3,5-dichlorophenyl | $CH_3$ |
| A-17 | 3-fluoro-5-methylphenyl | $CH_3$ |
| A-18 | 2-methoxy-5(trifluoromethyl)phenyl | $CH_3$ |

TABLE A-continued

| No. | ZR² | R¹ |
|---|---|---|
| A-19 | 3-chloro-5(trifluoromethyl)phenyl | CH₃ |
| A-20 | 3-(2-chloro-4-(trifluoromethyl)phenyl)phenyl | CH₃ |
| A-21 | 3-(2-chloro-4-(trifluoromethyl)phenyl)-4-fluorophenyl | CH₃ |
| A-22 | 3-(2-chloro-4-(trifluoromethyl)phenyl)-5-methylphenyl | CH₃ |
| A-23 | 3-phenylphenyl | CH₃ |
| A-24 | 4-methoxyphenyl | CH₃ |
| A-25 | 3-(3-chloro-5-trifluoromethyl-pyridine-2-yl)phenyl | CH₃ |
| A-26 | C₆H₅ | CH₂CH₃ |
| A-27 | 2-fluorophenyl | CH₂CH₃ |
| A-28 | 2-methoxyphenyl | CH₂CH₃ |
| A-29 | 2,4-difluorophenyl | CH₂CH₃ |
| A-30 | 2,6-difluorophenyl | CH₂CH₃ |
| A-31 | 4-fluorophenyl | CH₂CH₃ |
| A-32 | CO₂CH₂CH₃ | CH₂CH₃ |
| A-33 | C(O)CF₃ | CH₂CH₃ |
| A-34 | C(O)C₆H₅ | CH₂CH₃ |
| A-35 | 3-methoxyphenyl | CH₂CH₃ |
| A-36 | 3-cyanophenyl | CH₂CH₃ |
| A-37 | 3-(CO₂CH₂CH₃)phenyl | CH₂CH₃ |
| A-38 | 3-(C(O)N(CH₃)₂)phenyl | CH₂CH₃ |
| A-39 | 3-(trifluoromethyl)phenyl | CH₂CH₃ |
| A-40 | 3-(trifluoromethoxy)phenyl | CH₂CH₃ |
| A-41 | 3,5-dichlorophenyl | CH₂CH₃ |
| A-42 | 3-fluoro-5-methylphenyl | CH₂CH₃ |
| A-43 | 2-methoxy-5(trifluoromethyl)phenyl | CH₂CH₃ |
| A-44 | 3-chloro-5(trifluoromethyl)phenyl | CH₂CH₃ |
| A-45 | 3-(2-chloro-4-(trifluoromethyl)phenyl)phenyl | CH₂CH₃ |
| A-46 | 3-(2-chloro-4-(trifluoromethyl)phenyl)-4-fluorophenyl | CH₂CH₃ |
| A-47 | 3-(2-chloro-4-(trifluoromethyl)phenyl)-5-methylphenyl | CH₂CH₃ |
| A-48 | 3-phenylphenyl | CH₂CH₃ |
| A-49 | 4-methoxyphenyl | CH₂CH₃ |
| A-50 | 3-(3-chloro-5-trifluoromethyl-pyridine-2-yl-phenyl | CH₂CH₃ |
| A-51 | C₆H₅ | CH(CH₃)₂ |
| A-52 | 2-fluorophenyl | CH(CH₃)₂ |
| A-53 | 2-methoxyphenyl | CH(CH₃)₂ |
| A-54 | 2,4-difluorophenyl | CH(CH₃)₂ |
| A-55 | 2,6-difluorophenyl | CH(CH₃)₂ |
| A-56 | 4-fluorophenyl | CH(CH₃)₂ |
| A-57 | CO₂CH₂CH₃ | CH(CH₃)₂ |
| A-58 | C(O)CF₃ | CH(CH₃)₂ |
| A-59 | C(O)C₆H₅ | CH(CH₃)₂ |
| A-60 | 3-methoxyphenyl | CH(CH₃)₂ |
| A-61 | 3-cyanophenyl | CH(CH₃)₂ |
| A-62 | 3-(CO₂CH₂CH₃)phenyl | CH(CH₃)₂ |
| A-63 | 3-(C(O)N(CH₃)₂)phenyl | CH(CH₃)₂ |
| A-64 | 3-(trifluoromethyl)phenyl | CH(CH₃)₂ |
| A-65 | 3-(trifluoromethoxy)phenyl | CH(CH₃)₂ |
| A-66 | 3,5-dichlorophenyl | CH(CH₃)₂ |
| A-67 | 3-fluoro-5-methylphenyl | CH(CH₃)₂ |
| A-68 | 2-methoxy-5(trifluoromethyl)phenyl | CH(CH₃)₂ |
| A-69 | 3-chloro-5(trifluoromethyl)phenyl | CH(CH₃)₂ |
| A-70 | 3-(2-chloro-4-(trifluoromethyl)phenyl)phenyl | CH(CH₃)₂ |
| A-71 | 3-(2-chloro-4-(trifluoromethyl)phenyl)-4-fluorophenyl | CH(CH₃)₂ |
| A-72 | 3-(2-chloro-4-(trifluoromethyl)phenyl)-5-methylphenyl | CH(CH₃)₂ |
| A-73 | 3-phenylphenyl | CH(CH₃)₂ |
| A-74 | 4-methoxyphenyl | CH(CH₃)₂ |
| A-75 | 3-(3-chloro-5-trifluoromethyl-pyridine-2-yl-phenyl | CH(CH₃)₂ |
| A-76 | C₆H₅ | CH₂CH=CH₂ |
| A-77 | 2-fluorophenyl | CH₂CH=CH₂ |
| A-78 | 2-methoxyphenyl | CH₂CH=CH₂ |
| A-79 | 2,4-difluorophenyl | CH₂CH=CH₂ |
| A-80 | 2,6-difluorophenyl | CH₂CH=CH₂ |
| A-81 | 4-fluorophenyl | CH₂CH=CH₂ |
| A-82 | CO₂CH₂CH₃ | CH₂CH=CH₂ |
| A-83 | C(O)CF₃ | CH₂CH=CH₂ |
| A-84 | C(O)C₆H₅ | CH₂CH=CH₂ |
| A-85 | 3-methoxyphenyl | CH₂CH=CH₂ |
| A-86 | 3-cyanophenyl | CH₂CH=CH₂ |
| A-87 | 3-(CO₂CH₂CH₃)phenyl | CH₂CH=CH₂ |
| A-88 | 3-(C(O)N(CH₃)₂)phenyl | CH₂CH=CH₂ |
| A-89 | 3-(trifluoromethyl)phenyl | CH₂CH=CH₂ |
| A-90 | 3-(trifluoromethoxy)phenyl | CH₂CH=CH₂ |

TABLE A-continued

| No. | ZR² | R¹ |
|---|---|---|
| A-91 | 3,5-dichlorophenyl | CH$_2$CH=CH$_2$ |
| A-92 | 3-fluoro-5-methylphenyl | CH$_2$CH=CH$_2$ |
| A-93 | 2-methoxy-5(trifluoromethyl)phenyl | CH$_2$CH=CH$_2$ |
| A-94 | 3-chloro-5(trifluoromethyl)phenyl | CH$_2$CH=CH$_2$ |
| A-95 | 3-(2-chloro-4-(trifluoromethyl)phenyl)phenyl | CH$_2$CH=CH$_2$ |
| A-96 | 3-(2-chloro-4-(trifluoromethyl)phenyl)-4-fluorophenyl | CH$_2$CH=CH$_2$ |
| A-97 | 3-(2-chloro-4-(trifluoromethyl)phenyl)-5-methylphenyl | CH$_2$CH=CH$_2$ |
| A-98 | 3-phenylphenyl | CH$_2$CH=CH$_2$ |
| A-99 | 4-methoxyphenyl | CH$_2$CH=CH$_2$ |
| A-100 | 3-(3-chloro-5-trifluoromethyl-pyridine-2-yl)phenyl | CH$_2$CH=CH$_2$ |
| A-101 | C$_6$H$_5$ | CH$_2$C$_6$H$_5$ |
| A-102 | 2-fluorophenyl | CH$_2$C$_6$H$_5$ |
| A-103 | 2-methoxyphenyl | CH$_2$C$_6$H$_5$ |
| A-104 | 2,4-difluorophenyl | CH$_2$C$_6$H$_5$ |
| A-105 | 2,6-difluorophenyl | CH$_2$C$_6$H$_5$ |
| A-106 | 4-fluorophenyl | CH$_2$C$_6$H$_5$ |
| A-107 | CO$_2$CH$_2$CH$_3$ | CH$_2$C$_6$H$_5$ |
| A-108 | C(O)CF$_3$ | CH$_2$C$_6$H$_5$ |
| A-109 | C(O)C$_6$H$_5$ | CH$_2$C$_6$H$_5$ |
| A-110 | 3-methoxyphenyl | CH$_2$C$_6$H$_5$ |
| A-111 | 3-cyanophenyl | CH$_2$C$_6$H$_5$ |
| A-112 | 3-(CO$_2$CH$_2$CH$_3$)phenyl | CH$_2$C$_6$H$_5$ |
| A-113 | 3-(C(O)N(CH$_3$)$_2$)phenyl | CH$_2$C$_6$H$_5$ |
| A-114 | 3-(trifluoromethyl)phenyl | CH$_2$C$_6$H$_5$ |
| A-115 | 3-(trifluoromethoxy)phenyl | CH$_2$C$_6$H$_5$ |
| A-116 | 3,5-dichlorophenyl | CH$_2$C$_6$H$_5$ |
| A-117 | 3-fluoro-5-methylphenyl | CH$_2$C$_6$H$_5$ |
| A-118 | 2-methoxy-5(trifluoromethyl)phenyl | CH$_2$C$_6$H$_5$ |
| A-119 | 3-chloro-5(trifluoromethyl)phenyl | CH$_2$C$_6$H$_5$ |
| A-120 | 3-(2-chloro-4-(trifluoromethyl)phenyl)phenyl | CH$_2$C$_6$H$_5$ |
| A-121 | 3-(2-chloro-4-(trifluoromethyl)phenyl)-4-fluorophenyl | CH$_2$C$_6$H$_5$ |
| A-122 | 3-(2-chloro-4-(trifluoromethyl)phenyl)-5-methylphenyl | CH$_2$C$_6$H$_5$ |
| A-123 | 3-phenylphenyl | CH$_2$C$_6$H$_5$ |
| A-124 | 4-methoxyphenyl | CH$_2$C$_6$H$_5$ |
| A-125 | 3-(3-chloro-5-trifluoromethyl-pyridine-2-yl)phenyl | CH$_2$C$_6$H$_5$ |
| A-126 | C$_6$H$_5$ | CH$_2$CF$_3$ |
| A-127 | 2-fluorophenyl | CH$_2$CF$_3$ |
| A-128 | 2-methoxyphenyl | CH$_2$CF$_3$ |
| A-129 | 2,4-difluorophenyl | CH$_2$CF$_3$ |
| A-130 | 2,6-difluorophenyl | CH$_2$CF$_3$ |
| A-131 | 4-fluorophenyl | CH$_2$CF$_3$ |
| A-132 | CO$_2$CH$_2$CH$_3$ | CH$_2$CF$_3$ |
| A-133 | C(O)CF$_3$ | CH$_2$CF$_3$ |
| A-134 | C(O)C$_6$H$_5$ | CH$_2$CF$_3$ |
| A-135 | 3-methoxyphenyl | CH$_2$CF$_3$ |
| A-136 | 3-cyanophenyl | CH$_2$CF$_3$ |
| A-137 | 3-(CO$_2$CH$_2$CH$_3$)phenyl | CH$_2$CF$_3$ |
| A-138 | 3-(C(O)N(CH$_3$)$_2$)phenyl | CH$_2$CF$_3$ |
| A-139 | 3-(trifluoromethyl)phenyl | CH$_2$CF$_3$ |
| A-140 | 3-(trifluoromethoxy)phenyl | CH$_2$CF$_3$ |
| A-141 | 3,5-dichlorophenyl | CH$_2$CF$_3$ |
| A-142 | 3-fluoro-5-methylphenyl | CH$_2$CF$_3$ |
| A-143 | 2-methoxy-5(trifluoromethyl)phenyl | CH$_2$CF$_3$ |
| A-144 | 3-chloro-5(trifluoromethyl)phenyl | CH$_2$CF$_3$ |
| A-145 | 3-(2-chloro-4-(trifluoromethyl)phenyl)phenyl | CH$_2$CF$_3$ |
| A-146 | 3-(2-chloro-4-(trifluoromethyl)phenyl)-4-fluorophenyl | CH$_2$CF$_3$ |
| A-147 | 3-(2-chloro-4-(trifluoromethyl)phenyl)-5-methylphenyl | CH$_2$CF$_3$ |
| A-148 | 3-phenylphenyl | CH$_2$CF$_3$ |
| A-149 | 4-methoxyphenyl | CH$_2$CF$_3$ |
| A-150 | 3-(3-chloro-5-trifluoromethyl-pyridine-2-yl)phenyl | CH$_2$CF$_3$ |
| A-151 | 3-thienyl | CH$_3$ |
| A-152 | 3-thienyl | CH$_2$CH$_3$ |
| A-153 | 3-thienyl | CH(CH$_3$)$_2$ |
| A-154 | 3-thienyl | CH$_2$CH=CH$_2$ |
| A-155 | 3-thienyl | CH$_2$C$_6$H$_5$ |
| A-156 | 3-thienyl | CH$_2$CF$_3$ |
| A-157 | 2-thienyl | CH$_3$ |
| A-158 | 2-thienyl | CH$_2$CH$_3$ |
| A-159 | 2-thienyl | CH(CH$_3$)$_2$ |
| A-160 | 2-thienyl | CH$_2$CH=CH$_2$ |
| A-161 | 2-thienyl | CH$_2$C$_6$H$_5$ |
| A-162 | 2-thienyl | CH$_2$CF$_3$ |

TABLE A-continued

| No. | ZR² | R¹ |
|---|---|---|
| A-163 | 4-(2-methoxyethoxy)phenyl | $CH_3$ |
| A-164 | 4-(2-methoxyethoxy)phenyl | $CH_2CH_3$ |
| A-165 | 4-(2-methoxyethoxy)phenyl | $CH(CH_3)_2$ |
| A-166 | 4-(2-methoxyethoxy)phenyl | $CH_2CH=CH_2$ |
| A-167 | 4-(2-methoxyethoxy)phenyl | $CH_2C_6H_5$ |
| A-168 | 4-(2-methoxyethoxy)phenyl | $CH_2CF_3$ |
| A-169 | 2,4-dimethoxyphenyl | $CH_3$ |
| A-170 | 2,4-dimethoxyphenyl | $CH_2CH_3$ |
| A-171 | 2,4-dimethoxyphenyl | $CH(CH_3)_2$ |
| A-172 | 2,4-dimethoxyphenyl | $CH_2CH=CH_2$ |
| A-173 | 2,4-dimethoxyphenyl | $CH_2C_6H_5$ |
| A-174 | 2,4-dimethoxyphenyl | $CH_2CF_3$ |
| A-175 | 3-(m-tolylmethoxy)phenyl | $CH_3$ |
| A-176 | 3-(m-tolylmethoxy)phenyl | $CH_2CH_3$ |
| A-177 | 3-(m-tolylmethoxy)phenyl | $CH(CH_3)_2$ |
| A-178 | 3-(m-tolylmethoxy)phenyl | $CH_2CH=CH_2$ |
| A-179 | 3-(m-tolylmethoxy)phenyl | $CH_2C_6H_5$ |
| A-180 | 3-(m-tolylmethoxy)phenyl | $CH_2CF_3$ |
| A-181 | 4-isopropoxyphenyl | $CH_3$ |
| A-182 | 4-isopropoxyphenyl | $CH_2CH_3$ |
| A-183 | 4-isopropoxyphenyl | $CH(CH_3)_2$ |
| A-184 | 4-isopropoxyphenyl | $CH_2CH=CH_2$ |
| A-185 | 4-isopropoxyphenyl | $CH_2C_6H_5$ |
| A-186 | 4-isopropoxyphenyl | $CH_2CF_3$ |
| A-187 | 4-(2,4-difluorophenyl)phenyl | $CH_3$ |
| A-188 | 4-(2,4-difluorophenyl)phenyl | $CH_2CH_3$ |
| A-189 | 4-(2,4-difluorophenyl)phenyl | $CH(CH_3)_2$ |
| A-190 | 4-(2,4-difluorophenyl)phenyl | $CH_2CH=CH_2$ |
| A-191 | 4-(2,4-difluorophenyl)phenyl | $CH_2C_6H_5$ |
| A-192 | 4-(2,4-difluorophenyl)phenyl | $CH_2CF_3$ |
| A-193 | 4-(2-methoxyethoxy)phenyl | $CH_3$ |
| A-194 | 4-(2-methoxyethoxy)phenyl | $CH_2CH_3$ |
| A-195 | 4-(2-methoxyethoxy)phenyl | $CH(CH_3)_2$ |
| A-196 | 4-(2-methoxyethoxy)phenyl | $CH_2CH=CH_2$ |
| A-197 | 4-(2-methoxyethoxy)phenyl | $CH_2C_6H_5$ |
| A-198 | 4-(2-methoxyethoxy)phenyl | $CH_2CF_3$ |
| A-199 | 3-cyano-phenyl | $CH_3$ |
| A-200 | 3-cyano-phenyl | $CH_2CH_3$ |
| A-201 | 3-cyano-phenyl | $CH(CH_3)_2$ |
| A-202 | 3-cyano-phenyl | $CH_2CH=CH_2$ |
| A-203 | 3-cyano-phenyl | $CH_2C_6H_5$ |
| A-204 | 3-cyano-phenyl | $CH_2CF_3$ |
| A-205 | 3-fluorophenyl | $CH_3$ |
| A-206 | 3-fluorophenyl | $CH_2CH_3$ |
| A-207 | 3-fluorophenyl | $CH(CH_3)_2$ |
| A-208 | 3-fluorophenyl | $CH_2CH=CH_2$ |
| A-209 | 3-fluorophenyl | $CH_2C_6H_5$ |
| A-210 | 3-fluorophenyl | $CH_2CF_3$ |

The compound of formula (I) according to the present invention can be prepared according to the following syntheses routes, e.g. according to the preparation methods and preparation schemes as described below.

The compound of formula (I) according to the present invention can be prepared. According to the e.g. preparation methods and preparation schemes as described below.

The compounds used as starting materials for the syntheses of the compounds according to the present invention can generally be prepared by standard methods of organic chemistry. If not otherwise specified, the definitions of the variables such as X, Y, Het, $R^1$ and $R^2$ of the structures given in the schemes have the same meaning as defined above.

Compounds of the formula (I) can for example be prepared by reacting the appropriately substituted compounds P-1 with the a malonate derivative P-2 analogous to the methods described by Holyoke et al. in WO 2009/099929 (Scheme 1):

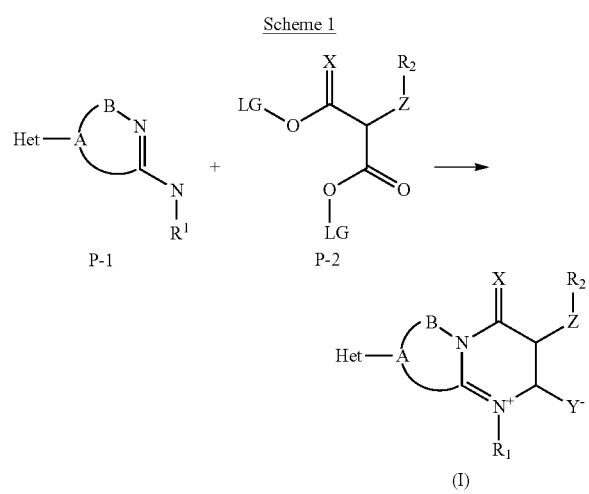

Compounds like P-1 can be prepared from the corresponding compounds P-3, by reacting it with an amine nucleophile like P-4 as described by, for example, Michel Langlois et al, Journal of Heterocyclic Chemistry, 19(1), 193-200; 1982, wherein LG denotes a leaving group such as halogen (e.g. chlorine or bromine), OR', or SR', with R' being $C_1$-$C_6$-alkyl, preferably chlorine methoxy ethoxy, methylthio or ethylthio (Scheme 2):

Scheme 2

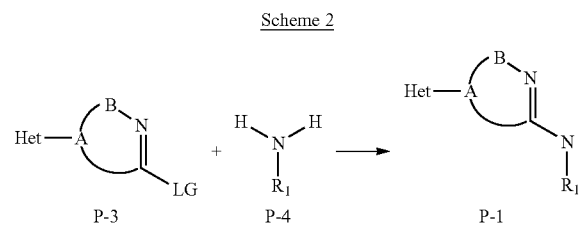

Compounds like P-3 are available from the corresponding lactams P-5 by standard procedures known to a person skilled in the art. For example see Allen, Jennifer Rebecca et al in WO 2004/094382 or Lang, Kai et al, Journal of Organic Chemistry, 75(19), 6424-6435; 2010 (Scheme 3):

Scheme 3

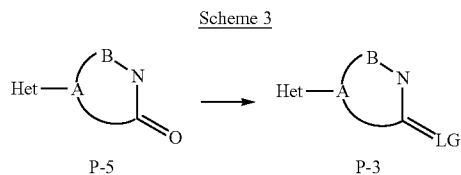

Lactams are widespread in organic chemistry and methods to produce them are well known. For example see: Smith, M. B. in Science of Synthesis, (2005) 21, 653.

If individual compounds cannot be prepared via the above described routes, they can be prepared by derivatization of other compounds of formula (I) or by customary modifications of the synthesis routes described.

For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or silica gel.

Mixtures

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin Scyclopentenyl, bioresmethrin, cycloprothrin, cyfluthrin, beta-cyfluthrin, cyhalothrin, lambdacyhalothrin, gamma-cyhalothrin, cypermethrin, alpha-cypermethrin, beta-cypermethrin, thetacypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.7B fenoxycarb or M.7C pyriproxyfen;

M.8 miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *bacillus thuringiensis* or *bacillus sphaericus* and the insecticidal proteins they produce such as *bacillus thuringiensis* subsp. *israelensis, bacillus sphaericus, bacillus thuringiensis* subsp. *aizawai, bacillus* thuringiensis subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.20B acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino] phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole, or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl] phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino) benzoyl]-1,2-dimethylhydrazinecarboxylate; or a compound selected from M.28.5a) to M.28.5d) and M.28.5h) to M.28.5l): M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl) pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl) pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl) amino]carbonyl]phenyl]-1H-pyrazole-5-carboxamide; M.28.5k) 3-Bromo-N-[2,4-dichloro-6-(methylcarbamoyl) phenyl]-1-(3,5-dichloro-2-pyridyl)-1H-pyrazole-5-carboxamide; M.28.5l) N-[4-Chloro-2-[[(1,1-dimethylethyl) amino]carbonyl]-6-methylphenyl]-1-(3-chloro-2-pyridinyl)-3-(fluoromethoxy)-1H-pyrazole-5-carboxamide; or M.28.6: cyhalodiamide; or;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1, 4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl) sulfinyl]phenyl]-3-(trifluoromethyl)-1H-1,2,4-triazole-5-amine, or actives on basis of *bacillus firmus* (Votivo, I-1582); or a compound selected from the group of M.29.6, wherein the compound is selected from M.29.6a) to M.29.6k): M.29.6a) (E/Z)—N-[1-[(6-chloro-3-pyridyl)methyl]-2- pyridylidene]-2,2,2-trifluoro-acetamide; M.29.6b) (E/Z)—N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)—N-[1-[(6-bromo-3-pyridyl)methyl]-2-pyridylidene]-2,2,2-trifluoro-acetamide; M.29.6e) (E/Z)—N-[1-[1-(6-chloro-3-pyridyl)ethyl]-2-pyridylidene]-2,2,2-trifluoro-acetamide; M.29.6f) (E/Z)—N-[1-[(6-chloro-3-pyridyl)methyl]-2-pyridylidene]-2,2-difluoro-acetamide; M.29.6g) (E/Z)-2-chloro-N-[1-[(6-chloro-3-pyridyl)methyl]-2-pyridylidene]-2,2-difluoro-acetamide; M.29.6h) (E/Z)—N-[1-[(2-chloropyrimidin-5-yl)methyl]-2-pyridylidene]-2,2,2-trifluoro-acetamide; M.29.6i) (E/Z)—N-[1-[(6-chloro-3-pyridyl)methyl]-2-pyridylidene]-2,2,3,3,3-pentafluoro-propanamide); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl)methyl]-2-pyridylidene]-2,2,2-trifluoro-N'-isopropyl-acetamidine; or the compounds M.29.8: fluazaindolizine; or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): fluxametamide; or M.29.10: 5-[3-[2,6-dichloro-4-(3,3-dichloroallyloxy)phenoxy]propoxy]-1H-pyrazole; or a compound selected from the group of M.29.11, wherein the compound is selected from M.29.11b) to M.29.11p):
M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.29.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; M.29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methylbenzamide; M.29.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methylbenzamide; M.29.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M.29.12, wherein the compound is selected from M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-Methylsulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide; M.29.12.f) N-Ethyl-N-[4-methyl-2-(3-pyridyl)thiazol-5-yl]-3-methyl-thio-propanamide; M.29.12.g) N-Methyl-N-[4-methyl-2-(3-pyridyl)thiazol-5-yl]-3-methylthio-propanamide; M.29.12.h) N,2-Dimethyl-N-[4-methyl-2-(3-pyridyl)thiazol-5-yl]-3-methylthio-propanamide; M.29.12.i) N-Ethyl-2-methyl-N-[4-methyl-2-(3-pyridyl)thiazol-5-yl]-3-methylthio-propanamide; M.29.12.j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methylthio-propanamide; M.29.12.m) N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitro-imidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide; M.29.16h) N-methyl-1-(2-fluoro-1-methyl-propyl)-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide, or M.29.17 a compound selected from the compounds M.29.17a) to M.29.17j): M.29.17a) N-(1-methylethyl)-2-(3-pyridinyl)-2H-indazole-4-carboxamide; M.29.17b) N-cyclopropyl-2-(3-pyridinyl)-2H-indazole-4-carboxamide; M.29.17c) N-cyclohexyl-2-(3-pyridinyl)-2H-indazole-4-carboxamide; M.29.17d) 2-(3-pyridinyl)-N-(2,2,2-trifluoroethyl)-2H-indazole-4-carboxamide; M.29.17e) 2-(3-pyridinyl)-N-[(tetrahydro-2-furanyl)methyl]-2H-indazole-5-carboxamide; M.29.17f) methyl 2-[[2-(3-pyridinyl)-2H-indazol-5-yl]carbonyl]hydrazinecarboxylate; M.29.17g) N-[(2,2-difluorocyclopropyl)methyl]-2-(3-pyridinyl)-2H-indazole-5-carboxamide; M.29.17h) N-(2,2-difluoropropyl)-2-(3-pyridinyl)-2H-indazole-5-carboxamide; M.29.17i) 2-(3-pyridinyl)-N-(2-pyrimidinylmethyl)-2H-indazole-5-carboxamide; M.29.17j) N-[(5-methyl-2-pyrazinyl)methyl]-2-(3-pyridinyl)-2H-indazole-5-carboxamide, or M.29.18 a compound selected from the compounds M.29.18a) to M.29.18d): M.29.18a) N-[3-chloro-1-(3-pyridyl)pyrazol-4-yl]-N-ethyl-3-(3,3,3-trifluoropropylsulfanyl)propanamide; M.29.18b) N-[3-chloro-1-(3-pyridyl) pyrazol-4-yl]-N-ethyl-3-(3,3,3-trifluoropropylsulfinyl) propanamide; M.29.18c) N-[3-chloro-1-(3-pyridyl)pyrazol-4-yl]-3-[(2,2-difluorocyclopropyl)methylsulfanyl]-N-ethyl-propanamide; M.29.18d) N-[3-chloro-1-(3-pyridyl)pyrazol-4-yl]-3-[(2,2-difluorocyclopropyl)methylsulfinyl]-N-ethyl-propanamide; or the compound M.29.19 sarolaner, or the compound M.29.20 lotilaner.

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compound M.28.6 can be found in WO2012/034472. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of bacillus firmus are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridyl-pyrazoles M.29.18a) to M.29.18d) are described in US2014/0213448. The isoxazoline M.29.19 is described in WO2014/036056. The isoxazoline M.29.20 is known from WO2014/090918.

The following list of fungicides, in conjunction with which the compounds of the present invention can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy. strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyltetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]-methyl]phenyl]-4-methyl-tetrazol-5-one (A.1.30), 1-[3-(difluoromethoxy)-2-[[2-methyl-4-(1-methyl-pyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl] phenyl]tetrazol-5-one (A.1.32), 1-methyl-4-[3-methyl-2-[[1-[3-(trifluoromethyl)phenyl]-ethylideneamino] oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluorophenyl)pyrazol-3-yl] oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-methoxypyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy) methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)phenyl)-1,3-dimethyl-5-fluoro-1H-pyrazole-4-carboxamide (A.3.20), 3-(difluoromethyl)-1 methyl-N-(1,1,3-trimethylindan-4-yl)pyrazole-4-carboxamide (A.3.21), 3-(trifluoromethyl)-1 methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e. g. complex I, uncouplers): diflumetorim (A.4.1), (5,8-difluoroquinazolin-4-yl)-{2-[2-fluoro-4-(4-trifluoromethyl pyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S,3R)-3-(2-chlorophenyl)-2-(2,4-difluorophenyl)-oxiranylmethyl]-5-thiocyanato-1H[1,2,4]triazolo (B.1.31), 2-[rel-(2S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.5l); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofosmethyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihyd ro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquatmethylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothalisopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethylisoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Formulations

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifi-ers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, al-kylated naphthalenes; alcohols, e.g. ethanol, propanol, butanol, benzylalcohol, cyclo¬hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl¬naphthalenes, sulfosuccinates or sulfosuccinamates. Examples of sulfates are sulfates of fatty acids and oils, of ethoxylated alkylphenols, of alcohols, of ethox-ylated alcohols, or of fatty acid esters. Examples of phosphates are phosphate esters. Exam-ples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Exam-ples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

Application Methods

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers;

eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, eucalyptus, flax, lentil, maize, melon, papaya, petunia, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1 Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including WideStrike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l anti-freezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

Pests

The compounds of the present invention are especially suitable for efficiently combating animal pests such as arthropods, gastropods and nematodes including but not limited to:

insects from the order of Lepidoptera, for example *Achroia grisella*, *Acleris* spp. such as *A. fimbriana*, *A. gloverana*, *A. variana*; *Acrolepiopsis assectella*, *Acronicta major*, *Adoxophyes* spp. such as *A. cyrtosema*, *A. orana*; *Aedia leucomelas*, *Agrotis* spp. such as *A. exclamationis*, *A. fucosa*, *A. ipsilon*, *A. orthogoma*, *A. segetum*, *A. subterranea*; *Alabama argillacea*, *Aleurodicus dispersus*, *Alsophila pometaria*, *Ampelophaga rubiginosa*, *Amyelois transitella*, *Anacampsis sarcitella*, *Anagasta kuehniella*, *Anarsia lineatella*, *Anisota senatoria*, *Antheraea pernyi*, *Anticarsia* (=*Thermesia*) *spp.* such as *A. gemmatalis*; *Apamea* spp., *Aproaerema modicella*, *Archips* spp. such as *A. argyrospila*, *A. fuscocupreanus*, *A. rosana*, *A. xyloseanus*; *Argyresthia conjugella*, *Argyroploce* spp., *Argyrotaenia* spp. such as *A. velutinana*; *Athetis mindara*, *Austroasca viridigrisea*, *Autographa gamma*, *Autographa nigrisigna*, *Barathra brassicae*, *Bedellia* spp., *Bonagota salubricola*, *Borbo cinnara*, *Bucculatrix thurberiella*, *Bupalus piniarius*, *Busseola* spp., *Cacoecia* spp. such as *C. murinana*, *C. podana*; *Cactoblastis cactorum*, *Cadra cautella*, *Calingo braziliensis*, *Caloptilis theivora*, *Capua reticulana*, *Carposina* spp. such as *C. niponensis*, *C. sasakii*; *Cephus* spp., *Chaetocnema aridula*, *Cheimatobia brumata*, *Chilo* spp. such as *C. Indicus*, *C. suppressalis*, *C. partellus*; *Choreutis pariana*, *Choristoneura* spp. such as *C. conflictana*, *C. fumiferana*, *C. longicellana*, *C. murinana*, *C. occidentalis*, *C. rosaceana*; *Chrysodeixis* (=*Pseudoplusia*) spp. such as *C. eriosoma*, *C. includens*; *Cirphis unipuncta*, *Clysia ambiguella*, *Cnaphalocerus* spp., *Cnaphalocrocis medinalis*, *Cnephasia* spp., *Cochylis hospes*, *Coleophora* spp., *Colias eurytheme*, *Conopomorpha* spp., *Conotrachelus* spp., *Copitarsia* spp., *Corcyra cephalonica*, *Crambus caliginosellus*, *Crambus teterrellus*, *Crocidosema* (=*Epinotia*) *aporema*, *Cydalima* (=*Diaphania*) *perspectalis*, *Cydia* (=*Carpocapsa*) spp. such as *C. pomonella*, *C. latiferreana*; *Dalaca noctuides*, *Datana integerrima*, *Dasychira pinicola*, *Dendrolimus* spp. such as *D. pini*, *D. spectabilis*, *D. sibiricus*, *Desmia funeralis*, *Diaphania* spp. such as *D. nitidalis*, *D. hyalinata*, *Diatraea grandiosella*, *Diatraea saccharalis*, *Diphthera festiva*, *Earias* spp. such as *E. insulana*, *E. vittella*, *Ecdytolopha aurantianu*, *Egira* (=*Xylomyges*) *curialis*, *Elasmopalpus iignosellus*, *Eldana saccharina*, *Endopiza viteana*, *Ennomos subsignaria*, *Eoreuma loftini*, *Ephestia* spp. such as *E. cautella*, *E. elutella*, *E. kuehniella*, *Epinotia aporema*, *Epiphyas postvittana*, *Erannis tiliaria*, *Erionota thrax*, *Etiella* spp., *Eulia* spp., *Eupoecilia ambiguella*, *Euproctis chrysorrhoea*, *Euxoa* spp., *Evetria bouliana*, *Faronta albilinea*, *Feltia* spp. such as *F. subterranean*, *Galleria mellonella*, *Gracillaria* spp., *Grapholita* spp. such as *G. funebrana*, *G. molesta*, *G. inopinata*; *Halysidota* spp., *Harrisina americana*, *Hedylepta* spp., *Helicoverpa* spp. such as *H. armigera* (=*Heliothis armigera*), *H. zea* (=*Heliothis zea*); *Heliothis* spp. such as *H. assulta*, *H. subflexa*, *H. virescens*; *Hellula* spp. such as *H. undalis*, *H. rogatalis*; *Helocoverpa gelotopoeon*, *Hemileuca oliviae*, *Herpetogramma licarsisalis*, *Hibernia defoliaria*, *Hofmannophila pseudospretella*, *Homoeosoma electellum*, *Homona magnanima*, *Hypena scabra*, *Hyphantria cunea*, *Hyponomeuta padella*, *Hyponomeuta malinellus*, *Kakivoria flavo fasciata*, *Keiferia lycopersicella*, *Lambdina fiscellaria fiscellaria*, *Lambdina fiscellaria lugubrosa*, *Lamprosema indicata*, *Laspeyresia molesta*, *Leguminivora glycinivorella*, *Lerodea eufala*, *Leucinodes orbonalis*, *Leucoma salicis*, *Leucoptera* spp. such as *L. coffeella*, *L. scitella*, *Leuminivora lycinivorella*, *Lithocolletis blancardella*, *Lithophane antennata*, *Llattia octo* (=*Amyna axis*), *Lobesia botrana*, *Lophocampa* spp., *Loxagrotis albicosta*, *Loxostege* spp. such as *L. sticticals*, *L. cereralis*, *Lymantria* spp. such as *L. dispar*, *L. monacha*, *Lyonetia cerkella*, *Lyonetia prunifoliella*, *Malacosoma* spp. such as *M. americanum*, *M. californicum*, *M. constrictum*, *M. neustria*; *Mamestra* spp. such as *M. brassicae*, *M. configurata*; *Mamstra brassicae*, *Manduca* spp. such as *M. quinquemaculata*, *M. sexta*; *Marasmia* spp, *Marmara* spp., *Maruca testulalis*, *Megalopyge lanata*, *Melanchra picta*, *Melanitis leda*, *Mocis* spp. such as *M. lapites*, *M. repanda*; *Mocis latipes*, *Monochroa fragariae*, *Mythimna separata*, *Nemapogon cloacella*, *Neoleucinodes* elegantalis, Nepytia spp., Nymphula spp., Oiketicus spp., Omiodes indicata, Omphisa anastomosalis, Operophtera brumata, Orgyia pseudotsugata, Oria spp., Orthaga thyrisalis, Ostrinia spp. such as O. nubilalis, Oulema oryzae, Paleacrita vernata, Panolis flammea, Parnara spp., Papaipema nebris, Papilio cresphontes, Paramyelois transitella, Paranthrene regalis, Paysandisia archon, Pectinophora spp. such as P. gossypiella, Peridroma saucia, Perileucoptera spp., such as P. coffeella, Phalera bucephala, Phryganidia californica, Phthorimaea spp. such as P. operculella, Phyllocnistis citrella, Phyllonorycter spp. such as P. blancardella, P. crataegella, P. issiki P. ringoniella, Pieris spp. such as P. brassicae, P. rapae, P. nap; Pilocrocis tripunctata, Plathypena scabra, Platynota spp. such as P. flavedana, P. idaeusalis, P. stultana; Platyptilia carduidactyla, Plebejus argus, Plodia interpunctella, Plusia spp, Plutella maculipennis, Plutella xylostella, Pontia protodica, Prays spp., Prodenia spp., Proxenus lepigone, Pseudaletia spp. such as P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius spp., Schreckensteinia festaliella, Scirpophaga spp. such as S. incertulas, S. innotata; Scotia segetum, Sesamia spp. such as S. inferens, Seudyra subflava, Sitotroga cerealella, Sparganothis pilleriana, Spilonota lechriaspis, S. ocellana, Spodoptera (=Lamphygma) spp. such as S. cosmoides, S. eridania, S. exigua, S. frugiperda, S. latisfascia, S. littoralis, S. litura, S. omithogalli; Stigmella spp., Stomopteryx subsecivella, Strymon bazochii, Sylepta derogata, Synanthedon spp. such as S. exitiosa, Tecia solanivora, Telehin licus, Thaumatopoea pityocampa, Thaumatotibia (=Cryptophlebia) leucotreta, Thaumetopoea pityocampa, Thecla spp., Theresimima ampelophaga, Thyrinteina spp, Tildenia inconspicuella, Tinea spp. such as T. cloacella, T. pellionella, Tineola bisselliella, Tortrix spp. such as T. viridana; Trichophaga tapetzella, Trichoplusia spp. such as T. ni; Tuta (=Scrobipalpula) absoluta, Udea spp. such as U. rubigalis, U. rubigalis; Virachola spp., Yponomeuta padella, and Zeiraphera canadensis;

insects from the order of Coleoptera, for example Acalymma vittatum, Acanthoscehdes obtectus, Adoretus spp., Agelastica alni, Agrilus spp. such as A. anxius, A. planipennis, A. sinuatus; Agriotes spp. such as A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora spp. such as A. glabripennis; Anthonomus spp. such as A. eugenii, A. grandis, A. pomorum; Anthrenus spp., Aphthona euphoridae, Apion spp., Apogonia spp., Athous haemorrhoidalis, Atomaria spp. such as A. linearis; Attagenus spp., Aulacophora femoralis, Blastophagus piniperda, Blitophaga undata, Bruchidius obtectus, Bruchus spp. such as B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus spp. such as C. assimilis, C. napi; Chaetocnema tibialis, Cleonus mendicus, Conoderus spp. such as C. vespertinus; Conotrachelus nenuphar, Cosmopolites spp., Costelytra zealandica, Crioceris asparag Cryptolestes ferrugineus, Cryptorhynchus lapathi, Ctenicera spp. such as C. destructor; Curculio spp., Cylindrocopturus spp., Cyclocephala spp., Dactylispa balyi, Dectes texanus, Dermestes spp., Diabrotica spp. such as D. undecimpunctata, D. speciosa, D. longicornis, D. semipunctata, D. virgifera; Diaprepes abbreviates, Dichocrocis spp., Dicladispa armigera, Diloboderus abderus, Diocalandra frumenti (Diocalandra stigmaticollis), Enaphalodes rufulus, Epilachna spp. such as E. varivestis, E. vigintioctomaculata, Epitrix spp. such as E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera spp. such as H. brunneipennis, H. postica; Hypomeces squamosus, Hypothenemus spp., Ips typographus, Lachnosterna consanguinea, Lasioderma serricorne, Latheticus oryzae, Lathridius spp., Lema spp. such as L. bilineata, L. melanopus; Leptinotarsa spp. such as L. decemlineata; Leptispa pygmaea, Limonius californicus, Lissorhoptrus oryzophilus, Lixus spp., Luperodes spp., Lyctus spp. such as L. bruneus, Liogenys fuscus, Macrodactylus spp. such as M. subspinosus; Maladera matrida, Megaplatypus mutates, Megascelis spp., Melanotus communis, Meligethes spp. such as M. aeneus; Melolontha spp. such as M. hippocastani, M. melolontha; Metamasius hemipterus, Microtheca spp., Migdolus spp. such as M. fryanus, Monochamus spp. such as M. alternatus, Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon spp. such as P. brassicae, P. cochleariae; Phoracantha recurva, Phyllobius pyri, Phyllopertha horticola, Phyllophaga spp. such as P. helleri, Phyllotreta spp. such as P. chrysocephala, P. nemorum, P. striolata, P. vittula; Phyllopertha horticola, Popillia japonica, Premnotrypes spp., Psacothea hilaris, Psylliodes chrysocephala, Prostephanus truncates, Psylliodes spp., Ptinus spp., Pulga saltona, Rhizopertha dominica, Rhynchophorus spp. such as R. billineatus, R. ferrugineus, R. palmarum, R. phoenicis, R. vulneratus; Saperda candida, Scolytus schevyrewi, Scyphophorus acupunctatus, Sitona lineatus, Sitophilus spp. such as S. granaria, S. oryzae, S. zeamais; Sphenophorus spp. such as S. levis; Stegobium paniceum, Sternechus spp. such as S. subsignatus; Strophomorphus ctenotus, Symphyletes spp., Tanymecus spp., Tenebrio molitor, Tenebrioides mauretanicus, Tribolium spp. such as T. castaneum; Trogoderma spp., Tychius spp., Xylotrechus spp. such as X. pyrrhoderus; and, Zabrus spp. such as Z. tenebrioides;

insects from the order of Diptera for example Aedes spp. such as A. aegypti, A. albopictus, A. vexans; Anastrepha ludens, Anopheles spp. such as A. albimanus, A. crucians, A. freeborni, A. gambiae, A. leucosphyrus, A. maculipennis, A. minimus, A. quadrimaculatus, A. sinensis, Bactrocera invadens, Bibio hortulanus, Calliphora erythrocephala, Calliphora vicina, Ceratitis capitata, Chrysomyia spp. such as C. bezziana, C. hominivorax, C. macellaria; Chrysops atlanticus, Chrysops discalis, Chrysops silacea, Cochliomyia spp. such as C. hominivorax; Contarinia spp. such as C. sorghicola; Cordylobia anthropophaga, Culex spp. such as C. nigripalpus, C. pipiens, C. quinquefasciatus, C. tarsalis, C. tritaeniorhynchus; Culicoides furens, Culiseta inornata, Culiseta melanura, Cuterebra spp., Dacus cucurbitae, Dacus oleae, Dasineura brassicae, Dasineura oxycoccana, Delia spp. such as D. antique, D. coarctata, D. platura, D. radicum; Dermatobia hominis, Drosophila spp. such as D. suzuki/Fannia spp. such as F. canicularis; Gastraphilus spp. such as G. intestinalis, Geomyza tipunctata, Glossina spp. such as G. fuscipes, G. morsitans, G. palpalis, G. tachinoides; Haematobia irritans, Haplodiplosis equestris, Hippelates spp., Hylemyia spp. such as H. platura; Hypoderma spp. such as H. lineata; Hyppobosca spp., Hydrellia philippina, Leptoconops torrens, Liriomyza spp. such as L. sativae, L. trifolii; Lucilia spp. such as L. caprina, L. cuprina, L. sericata; Lycoria pectorails, Mansonia titillanus, Mayetiola spp. such as M. destructor Musca spp. such as M. autumnails, M domestica; Muscina stabulans, Oestrus spp. such as O. ovis; Opomyza florum, Oscinella spp. such as O. frit; Orseolia oryzae, Pegomya hysocyami, Phlebotomus argentipes, Phorbia spp. such as P. antiqua, P. brassicae, P. coarctata; Phytomyza gymnostoma, Prosimulium mixtum, Psila rosae, Psorophora columbiae, Psorophora discolor, Rhagoletis spp. such as R. ceras; R. cingulate, R. indifferens, R. mendax, R. pomonella, Rivellia quadrifasciata, Sarcophaga spp. such as S. haemorrhoidalis; Simulium vittatum, Sitodiplosis mosellana, Stomoxys spp. such as S. calcitrans; Tabanus spp. such as T. atratus, T. bovinus, T. lineola, T. similis; Tannia spp., Thecodiplosis japonensis, Tipula oleracea, Tipula paludosa, and Wohlfahrtia spp;

insects from the order of Thysanoptera for example, Baliothrips biformis, Dichromothrips corbetti Dichromothrips ssp., Echinothrips americanus, Enneothrips flavens, Frankliniella spp. such as F. fusca, F. occidentalis, F. tritici, Heliothrips spp., Hercinothrips femoralis, Kakothrips spp., Microcephalothrips abdominalis, Neohydatothrips samayunkur, Pezothrips kellyanus, Rhipiphorothrips cruentatus, Scirtothrips spp. such as S. citri, S. dorsalis, S. perseae; Stenchaetothrips spp, Taeniothrips cardamoni, Taeniothrips inconsequens, Thrips spp. such as T. imagines, T. hawaiiensis, T. oryzae, T. palmi T. parvispinus, T. tabaci;

insects from the order of Hemiptera for example, Acizzia jamatonica, Acrosternum spp. such as A. hilare; Acyrthosipon spp. such as A. onobrychis, A. pisum; Adelges laricis, Adelges tsugae, Adelphocoris spp., such as A. rapidus, A. superbus; Aeneolamia spp., Agonoscena spp., Aulacorthum solani, Aleurocanthus woglumi, Aleurodes spp., Aleurodicus disperses, Aleurolobus barodensis, Aleurothrixus spp., Amrasca spp., Anasa tristis, Antestiopsis spp., Anuraphis cardui, Aonidiella spp., Aphanostigma piri, Aphidula nasturtii, Aphis spp. such as A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella spp., Aspidiotus spp., Atanus spp., Aulacaspis yasumatsui, Aulacorthum solani, Bactericera cockerelli (Paratrioza cockerelli), Bemisia spp. such as B. argentifolii, B. tabaci (Aleurodes tabaci); Blissus spp. such as B. leucopterus, Brachycaudus spp. such as B. cardui, B. helichrysi, B. persicae, B. prunicola; Brachycolus spp., Brachycorynella asparagi, Brevicoryne brassicae, Cacopsylla spp. such as C. fulguralis, C. pyricola (Psylla piri); Calligypona marginata, Calocoris spp., Campylomma livida, Capitophorus horni, Carneocephala fulgida, Caveleriellus spp., Ceraplastes spp., Ceratovacuna lanigera, Ceroplastes ceriferus, Cerosipha gossypii, Chaetosiphon fragaefolii, Chionaspis tegalensis, Chlorita onuki, Chromaphis juglandicola, Chrysomphalus ficus, Cicadulina mbila, Cimexspp. such as C. hemipterus, C. lectularius; Coccomytilus halli, Coccus spp. such as C. hesperidum, C. pseudomagnoliarum; Corythucha arcuata, Creontiades dilutus, Crypto myzus ribis, Chrysomphalus aonidum, Cryptomyzus ribis, Ctenarytaina spatulata, Cyrtopeltis notatus, Dalbulus spp., Dasynus piperis, Dialeurodes spp. such as D. citrifolii Dalbulus maidis, Diaphorina spp. such as D. citri; Diaspis spp. such as D. bromeliae, Dichelops furcatus, Diconocoris hewetti, Doralis spp., Dreyfusia nordmannianae, Dreyfusia piceae, Drosicha spp., Dysaphis spp. such as D. plantaginea, D. pyri, D. radicola; Dysaulacorthum pseudosolani, Dysdercus spp. such as D. cingulatus, D. intermedius, Dysmicoccus spp., Edessa spp., Geocoris spp., Empoasca spp. such as E. fabae, E. solana, Epidiaspis leperii, Eriosoma spp. such as E. lanigerum, E. pyricola; Erythroneura spp., Eurygaster spp. such as E. integriceps; Euscelis bilobatus, Euschistus spp. such as E. heros, E. impictiventris, E. servus; Fiorinia theae, Geococcus coffeae, Glycaspis brimblecombei, Halyomorpha spp. such as H. halys; Heliopeltis spp., Homalodisca vitripennis (=H. coagulata), Horcias nobilellus, Hyalopterus pruni, Hyperomyzus lactucae, Icerya spp. such as I. purchase; diocerus spp., Idioscopus spp., Laodelphax striatellus, Lecanium spp., Lecanoideus floccissimus, Lepidosaphes spp. such as L. ulmi, Leptocorisa spp., Leptoglossus phyllopus, Lipaphis erysimi, Lygus spp. such as L. hesperus, L. lineolaris, L. pratensis; Maconellicoccus hirsutus, Marchalina hellenica, Macropes excavatus, Macrosiphum spp. such as M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) caryaefoliae, Metcafiella spp., Metopolophium dirhodum, Monellia costalis, Monelliopsis pecanis, Myzocallis coryli, Murgantia spp., Myzus spp. such as M. ascalonicus, M. cerasi, M. nicotianae, M. persicae, M. varians; Nasonovia ribis-nigri, Neotoxoptera formosana, Neomegalotomus spp, Nephotettix spp. such as N. malayanus, N. nigropictus, N. parvus, N. virescens; Nezara spp. such as N. viridula; Nilaparvata lugens, Nysius huttoni, Oebalus spp. such as O. pugnax; Oncometopia spp., Orthezia prae longa, Oxycaraenus hyalinipennis, Parabemisia myricae, Parlatoria spp., Parthenolecanium spp. such as P. corni, P. persicae; Pemphigus spp. such as P. bursarius, P. populivenae; Peregrinus maidis, Perkinsiella saccharicida, Phenacoccus spp. such as P. aceris, P. gossypii Phloeomyzus passerinii, Phorodon humuli, Phylloxera spp. such as P. devastatrix, Piesma quadrata, Piezodorus spp. such as P. guildini Pinnaspis aspidistrae, Planococcus spp. such as P. citri, P. ficus; Prosapia bicincta, Protopulvinaria pyriformis, Psallus seriatus, Pseudacysta persea, Pseudaulacaspis pentagona, Pseudococcus spp. such as P. comstocki, Psylla spp. such as P. mali, Pteromalus spp., Pulvinaria amygdali, Pyrilla spp., Quadraspidiotus spp., such as Q. perniciosus; Quesada gigas, Rastrococcus spp., Reduvius senilis, Rhizoecus americanus, Rhodnius spp., Rhopalomyzus ascalonicus, Rhopalosiphum spp. such as R. pseudobrassicas, R. insertum, R. maidis, R. padi, Sagatodes spp., Sahlbergella singularis, Saissetia spp., Sappaphis mala, Sappaphis mali, Scaptocoris spp., Scaphoides titanus, Schizaphis graminum, Schizoneura lanuginosa, Scotinophora spp., Selenaspidus articulatus, Sitobion avenae, Sogata spp., Sogatella furcifera, Solubea insularis, Spissistilus festinus (=Stictocephala festina), Stephanitis nashi, Stephanitis pyrioides, Stephanitis takeyai, Tenalaphara malayensis, Tetraleurodes perseae, Therioaphis maculate, Thyanta spp. such as T. accerra, T. perditor Tibraca spp., Tomaspis spp., Toxoptera spp. such as T. auranti Trialeurodes spp. such as T. abutilonea, T. ricini, T. vaporariorum; Triatoma spp., Trioza spp., Typhlocyba spp., Unaspis spp. such as U. citri, U. yanonensis; and Viteus vitifolii, Insects from the order Hymenoptera for example Acanthomyops interjectus, Athalia rosae, Atta spp. such as A. capiguara, A. cephalotes, A. cephalotes, A. laevigata, A. robusta, A. sexdens, A. texana, Bombus spp., Brachymyrmex spp., Camponotus spp. such as C. floridanus, C. pennsylvanicus, C. modoc; Cardiocondyla nuda, Chalibion sp, Crematogaster spp., Dasymutilla occidentalis, Diprion spp., Dolichovespula maculata, Dorymyrmex spp., Dryocosmus kuriphilus, Formica spp., Hoplocampa spp. such as H. minuta, H. testudinea; Iridomyrmex humilis, Lasius spp. such as L. niger, Linepithema humile, Liometopum spp.,

*Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S. invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal, Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. ameri cana, S. gregaria, Stemopelmatus* spp., *Tachycines asynamorus*, and *Zonozerus variegatus;*

Pests from the Class Arachnida for example *Acari*, e.g. of the families Argasidae, Ixodidae and Sarcoptidae, such as *Amblyomma* spp. (e.g. *A. americanum, A. variegatum, A. maculatum), Argas* spp. such as *A. persicu), Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. Scabiei*, and Family Eriophyidae including *Aceria* spp. such as *A. sheldoni, A. anthocoptes, Acallitus* spp., *Aculops* spp. such as *A. lycopersici, A. pelekass, Aculus* spp. such as *A. schlechtendali; Colomerus vitis, Epitrimerus pyri, Phyllocoptruta oleivora; Eriophytes ribis* and *Eriophyes* spp. such as *Eriophyes sheldon,*

Family Tarsonemidae including *Hemitarsonemus* spp., *Phytonemus pallidus* and *Polyphagotarsonemus latus, Stenotarsonemus* spp. *Steneotarsonemus spink*, Family Tenuipalpidae including *Brevipalpus* spp. such as *B. phoenicis;* Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T. pacificus, T. phaseulus, T. telarius* and *T. urticae; Bryobia praetiosa; Panonychus* spp. such as *P. ulmi, P. citri, Metatetranychus* spp. and *Oligonychus* spp. such as *O. pratensis, O. perseae, Vasates lycopersici; Raoiella indica,* Family Carpoglyphidae including *Carpoglyphus* spp., *Penthaleidae* spp. such as *Halotydeus destructor*, Family Demodicidae with species such as *Demodex* spp.; Family Trombicidea including *Trombicula* spp.; Family Macronyssidae including *Ornothonyssus* spp.; Family Pyemotidae including *Pyemotes tritic, Tyrophagus putrescentiae;* Family Acaridae including *Acarus siro;* Family Araneida including *Latrodectus mactans, Tegenaria agrestis, Chiracanthium* sp, *Lycosa* sp *Achaearanea tepidariorum* and *Loxosceles reclusa*

Pests from the Phylum Nematoda, for example, plant parasitic nematodes such as root-knot nematodes, *Meloidogyne* spp. such as *M. hapla, M. incognita, M. javanica;* cyst-forming nematodes, *Globodera* spp. such as *G. rostochiensis; Heterodera* spp. such as *H. avenae, H. glycines, H. schachtii, H. trifolii;* Seed gall nematodes, *Anguina* spp.; Stem and foliar nematodes, *Aphelenchoides* spp. such as *A. besseyi*, Sting nematodes, *Belonolaimus* spp. such as *B. longicaudatus;* Pine nematodes, *Bursaphelenchus* spp. such as *B. lignicolus, B. xylophilus;* Ring nematodes, *Criconema* spp., *Criconemella* spp. such as *C. xenoplax* and *C. ornata;* and, *Criconemoides* spp. such as *Criconemoides informis; Mesocriconema* spp.; Stem and bulb nematodes, *Ditylenchus* spp. such as *D. destructor, D. dipsaci,* Awl nematodes, *Dolichodorus* spp.; Spiral nematodes, *Heliocotylenchus multicinctus;* Sheath and sheathoid nematodes, *Hemicycliophora* spp. and *Hemicriconemoides* spp., *Hirshmanniella* spp.; Lance nematodes, *Hoploaimus* spp.; False rootknot nematodes, *Nacobbus* spp.; Needle nematodes, *Longidorus* spp. such as *L. elongatus;* Lesion nematodes, *Pratylenchus* spp. such as *P. brachyurus, P. neglectus, P. penetrans, P. curvitatus, P. goodeyi;* Burrowing nematodes, *Radopholus* spp. such as *R. similis; Rhadopholus* spp., *Rhodopholus* spp., Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor;* Stunt nematodes, *Tylenchorhynchus* spp. such as *T. claytoni, T. dubius;* Citrus nematodes, *Tylenchulus* spp. such as *T. semipenetrans;* Dagger nematodes, *Xiphinema* spp.; and other plant parasitic nematode species;

Insects from the order Isoptera for example *Calotermes flavicollis, Coptotermes* spp. such as *C. formosanus, C. gestroi, C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor, I. Snyder, Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus; Termes natalensis,*

Insects from the order Blattaria for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis,*

Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans*, and *Nosopsyllus fasciatus,*

Insects from the order Thysanura for example *Lepisma saccharina, Ctenolepisma urbana*, and *Thermobia domestica,*

Pests from the class Chilopoda for example *Geophilus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forficula auricularia,*

Insects from the order Collembola, for example *Onychiurus* spp., such as *Onychiurus armatus,*

Pests from the order Isopoda for example, *Armadillidium vulgare, Oniscus asellus, Porcellio scaber,*

Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi Trichinella nelson, Trichinella pseudopsiralis, Trichostrongulus* spp., *Trichuris trichiura, Wuchereria bancrofti.*

Animal Health

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a non-therapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*; cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigrpalpus, Culex quinquefasciatus, Culex tarsalis, Culiseta inornata, Culiseta melanura, Dermatobia hominis, Fannia canicularis, Gas-* terophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola, and Tabanus similis; lice (Phthiraptera), e.g. Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capillatus, ticks and parasitic mites (Parasitiformes): ticks (Ixodida), e.g. Ixodes scapularis, Ixodes holocyclus, Ixodes pacificus, Rhiphicephalus sanguineus, Dermacentor anderson/Dermacentor variabilis, Amblyomma americanum, Ambryomma maculatum, Ornithodorus hermsi, Ornithodorus turicata and parasitic mites (Mesostigmata), e.g. Omithonyssus bacoti and Dermanyssus gallinae; Actinedida (Prostigmata) und Acaridida (Astigmata), e.g. Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., and Laminosioptes spp; Bugs (Heteropterida): Cimex lectularius, Cimex hemipterus, Reduvius senilis, Triatoma spp., Rhodnius ssp., Panstrongylus ssp., and Arilus critatus; Anoplurida, e.g. Haematopinus spp., Linognathus spp., Pediculus spp., Phtirus spp., and Solenopotes spp., Mallophagida (suborders Arnblycerina and Ischnocerina), e.g. Trimenopon spp., Menopon spp., Trinoton spp., Bovicola spp., Werneckiella spp., Lepikentron spp., Trichodectes spp., and Felicola spp., Roundworms Nematoda: Wipeworms and Trichinosis (Trichosyringida), e.g. Trichinellidae (Trichinella spp.), (Trichuridae) Trichuris spp., Capillaria spp., Rhabditida, e.g. Rhabditis spp., Strongyloides spp., Helicephalobus spp., Strongylida, e.g. Strongylus spp., Ancylostoma spp., Necator americanus, Bunostomum spp. (Hookworm), Trichostrongylus spp., Haemonchus contortus, Ostertagia spp., Cooperia spp., Nematodirus spp., Dictyocaulus spp., Cyathostoma spp., Oesophagostomum spp., Stephanurus dentatus, Ollulanus spp., Chabertia spp., Stephanurus dentatus, Syngamus trachea, Ancylostoma spp., Uncinaria spp., Globocephalus spp., Necator spp., Metastrongylus spp., Muellerius capillaris, Protostrongylus spp., Angiostrongylus spp., Parelaphostrongylus spp., Aleurostrongylus abstrusus, and Dioctophyma renale; Intestinal roundworms (Ascaridida), e.g. Ascaris lumbricoides, Ascaris suum, Ascaridia galli, Parascaris equorum, Enterobius vermicularis (Threadworm), Toxocara canis, Toxascaris leonine, Skrjabinema spp., and Oxyuris equi, Camallanida, e.g. Dracunculus medinensis (guinea worm); Spirurida, e.g. Thelazia spp., Wuchereria spp., Brugia spp., Onchocerca spp., Dirofilari spp.a, Dipetalonema spp., Setaria spp., Elaeophora spp., Spirocerca lupi, and Habronema spp.; Thorny headed worms (Acanthocephala), e.g. Acanthocephalus spp., Macracanthorhynchus hirudinaceus and Oncicola spp., Planarians (Plathelminthes): Flukes (Trematoda), e.g. Faciola spp., Fascioloides magna, Paragonimus spp., Dicrocoelium spp., Fasciolopsis buski, Clonorchis sinensis, Schistosoma spp., Trichobilharzia spp., Alaria alata, Paragonimus spp., and Nanocyetes spp.; Cercomeromorpha, in particular Cestoda (Tapeworms), e.g. Diphyllobothrium spp., Tenia spp., Echinococcus spp., Dipylidium caninum, Multiceps spp., Hymenolepis spp., Mesocestoides spp., Vampirolepis spp., Moniezia spp., Anoplocephala spp., Sirometra spp., Anoplocephala spp., and Hymenolepis spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

The present invention is now illustrated in further details by the following examples, without imposing any limitation thereto.

EXAMPLES

Example Compound C-1

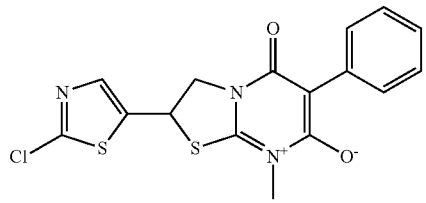 [SMILES: C[n+]1c([O-])c(-c2ccccc2)c(=O)n2c1SC(c1cnc(Cl)s1)C2]

Characterization ($^1$H-NMR): CDCl$_3$/ppm/400 MHz)
7.76 (d, 2H), 7.54 (s, 1H), 7.37 (t, 2H), 7.21 (t, 1H), 5.26 (t, 1H), 4.96 (q, 1H), 4.53 (q, 1H), 3.49 (s, 3H)

Further Examples

Procedure of Synthesis for Example 11:

To a stirred solution of 2-chlorothiazole E-1 (80 g) in anhydrous THF (1000 mL) was added nBuLi (320 mL, 0.8 mol) drop wise at −78° C. for one hour. Ethyl formate (74 g) was added dropwise to the solution at −78° C., and stirred for one additional hour. Saturated NH$_4$Cl was added to the reaction mixture and stirred for 30 min, then diluted with ethyl acetate. The aqueous phase was extracted with ethyl acetate. The organic phase was washed and dried, then concentrated to give the crude product, which was purified by re-crystallized with hexane/ethyl acetate to give 2-chlorothiazole-5-carbaldehyde E-2 (72 g yield: 73%); 1H NMR (400 MHz, CDCl$_3$): δ ppm 9.96 (s., 1H), 8.21 (s, 1H).

To a stirred solution of 2-chlorothiazole-5-carbaldehyde E-2 (23.3 g) in acetonitrile (500 mL) was added nitromethane (38.6 g), followed by DBU (36.3 g) at 0° C. The solution was stirred for 3 hours at 0° C. To the reaction mixture, 1.5N HCl (50 ml) was added, then extracted with ethyl acetate. The organic phase was washed and dried, then concentrated to give the crude product, which was purified by column chromatography to afford pure 1-(2-chlorothiazol-5-yl)-2-nitro-ethanol E-3 (17.3 g, yield: 52.3%); 1H NMR (400 MHz, CDCl$_3$): δ ppm 3.60 (br. S, 1H), 4.58-4.76 (m, 2H), 5.72 (dd, J=8.91, 3.14 Hz, 1H), 7.42-7.54 (m, 1H)

To a solution of 1-(2-chlorothiazol-5-yl)-2-nitro-ethanol E-3 (17.3 g) in ethanole (550 mL) and water (180 mL) was added NH$_4$Cl (44.9 g, 832 mmol), followed by Fe powder (46.6 g) at 18° C. in portions over an hour. The solution was heated at 100° C. for 16 hours. The reaction mixture was cooled to room temperature and the dark solution was filtered through a pad of celite, and the filter cake was washed with EtOH. The filtrate was concentrated in vacuo, then dissolved in water (100 ml) and extracted with ethyl acetate, the aqueous layer was extracted with DCM: IPA (3:1). The organic layers were combined, dried, filtered and concentrated to give the crude product 2-amino-1-(2-chlorothiazol-5-yl)ethanol E-4 (6.3 g, yield: 42.6%), which was taken to next step without purification.

To a stirred solution of 2-amino-1-(2-chlorothiazol-5-yl) ethanol E-4 (6.3 g, 35.4 mmol) in anhydrous EtOH (300 mL) was added TEA (7.15 g, 70.8 mmol), followed by methyl isothiocyanate (5.45 g, 70.8 mmol) at 0° C. The reaction mixture was stirred at 18° C. for 16 hours. The reaction mixture was concentrated in vacuo and then dissolved in ethyl acetate and washed with water. The combined organic layer was washed, filtered and concentrated to give the crude product 1-[2-(2-chlorothiazol-5-yl)-2-hydroxy-ethyl]-3-methyl-thiourea E-5, which was purified by column to afford as yellow solid (5.5 g, yield: 61.9%). 1H NMR (400 MHz, MeOD): δ ppm 2.95 (d, J=9.29 Hz, 3H), 3.65-3.90 (m, 2H), 5.19 (s., 1H), 7.41-7.55 (m, 1H).

To a solution of 1-[2-(2-chlorothiazol-5-yl)-2-hydroxy-ethyl]-3-methyl-thiourea E-5 (5.5 g) in anhydrous THF (150 mL) was added CDI (5.3 g, 32.9 mmol) at 0° C. The reaction mixture solution was stirred at 15° C. for 16 hours. Water was added, and the reaction mixture was extracted with ethyl acetate. The organic phase was washed, filtered and concentrated to give the crude product. The crude product was purified by column to afford 5-(2-chlorothiazol-5-yl)-N-methyl-4,5-dihydrothiazol-2-amine E-6 (2 g, yield: 39.2%) as a white solid; 1H NMR (400 MHz, CDCl$_3$): δ ppm 2.95-3.03 (m, 3H), 4.09 (dd, J=13.55, 4.77 Hz, 1H), 4.32 (dd, J=13.55, 7.03 Hz, 1H), 5.14 (dd, J=7.03, 4.77 Hz, 1H), 7.40 (s, 1H).

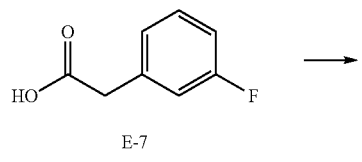

E-7

2-(3-fluorophenyl)acetic acid

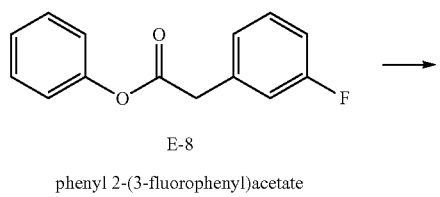

E-8 phenyl 2-(3-fluorophenyl)acetate

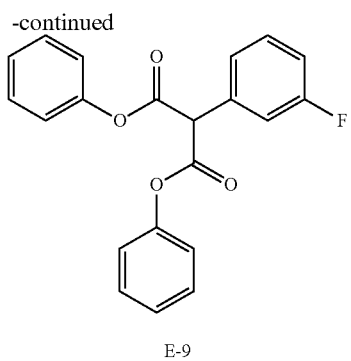

E-9 diphenyl 2-(3-fluorophenyl)propanedioate

To a solution of 2-(3-fluorophenyl)acetic acid E-7 (1 g) in anhydrous CH$_2$Cl$_2$ (50 mL) was added phenol (0.66 g), DCC (1.6 g) and catalytic amount of DMAP. The reaction mixture was stirred at room temperature (20-25° C.) for 16 hours. The mixture was filtered and diluted with CH$_2$Cl$_2$, then washed with water. The organic layers were concentrated, and the residue was purified by silica gel column chromatography (hexane/ethyl acetate) to afford the product phenyl 2-(3-fluorophenyl)acetate E-8 as oily liquid (0.850 g Yield: 57%); 1H NMR—(400 MHz, CDCl$_3$): δ ppm 7.31 (m, 2H), 7.29-6.90 (m, 9H), 3.78 (s, 2H)

To a solution of phenyl 2-(3-fluorophenyl)acetate E-8 (1 g) in anhydrous THF (50 mL) was added lithium hexamethyldisilane (10.8 ml) at −78° C. After an hour, phenyl chloroformate (1.2 eq) was added, and the reaction mixture was stirred at the same temperature for an hour. Saturated NH$_4$Cl solution was added, and the mixture was diluted and extracted with ethyl acetate. The organic layers were concentrated, and the resulting residue was purified by silica flash column chromatography (hexane/ethyl acetate) to afford the product diphenyl 2-(3-fluorophenyl)propanedioate E-9 as oily liquid (0.850 g Yield: 57%.)

1H NMR—(400 MHz, CDCl$_3$): δ ppm 7.32 (m, 4H), 7.29-6.90 (m, 14H), 5.72 (s, 1H)

To a solution of 5-(2-chlorothiazol-5-yl)-N-methyl-4,5-dihydrothiazol-2-amine E-6 (0.250 g) in anhydrous toluene (50 mL) was added diphenyl 2-(3-fluorophenyl)propanedioate E-9 (0.424 g), and the mixture was heated at 120° C., for 12 hours. The mixture was cooled to room temperature and triturated with MTBE. The solid was filtered through a sintered funnel to get the crude product as an off-white solid. The crude product was recrystallized with MTBE to afford the example compound 11 as pale yellow solid (0.210 g Yield: 50%.)

1H NMR—(400 MHz, CDCl$_3$): δ ppm 9.34 (s, 1H), 7.86 (m, 2H), 7.63 (m, 1H), 6.93 (m, 1H), 5.80 (t, 1H), 4.84 (m, 2H), 2H).

By analogous procedures to the procedure described above for example 11, the following examples of formula I-ex were prepared, wherein the substituents Het, Z—R$^2$ and R$^1$ are as depicted in the table and wherein "*" denotes the attachment site.

I-ex

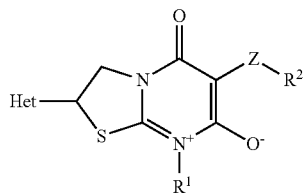

| Example No | Het | Z—R² | R¹ | Physicochemical data: HPLC-Retention [min] |
|---|---|---|---|---|
| 1 = C-1 | 2-Cl-thiazol-5-yl | phenyl | CH₃ | t = 0.815 (MS [m/z]: 377.9) [A] |
| 2 | 6-Cl-pyridin-3-yl | 3,5-dichlorophenyl | CH₃ | t = 1.058 (MS [m/z]: 441.9) [A] |
| 3 | 2-Cl-thiazol-5-yl | 3,5-dichlorophenyl | CH₃ | t = 1.083 (MS [m/z]: 447.8) [A] |
| 4 | 2-Cl-thiazol-5-yl | 4-OCH₃-phenyl | CH₃ | t = 0.824 (MS [m/z]: 407.9) [A] |
| 5 | 2-Cl-thiazol-5-yl | 3-CF₃-phenyl | CH₃ | t = 1.018 (MS [m/z]: 445.9) [A] |
| 6 | 6-Cl-pyridin-3-yl | phenyl | CH₃ | t = 0.797 (MS [m/z]: 371.9) [A] |
| 7 | 6-Cl-pyridin-3-yl | 4-OCH₃-phenyl | CH₃ | t = 0.806 (MS [m/z]: 401.9) [A] |
| 8 | 6-Cl-pyridin-3-yl | 3-CF₃-phenyl | CH₃ | t = 0.998 (MS [m/z]: 439.9) [A] |
| 9 | 2-Cl-thiazol-5-yl | thiophen-3-yl | CH₃ | t = 1.235 (MS [m/z]: 384.0) [B] |
| 10 | 2-Cl-thiazol-5-yl | thiophen-2-yl | CH₃ | t = 2.127 (MS [m/z]: 384.0) [C] |
| 11 | 2-Cl-thiazol-5-yl | 3-F-phenyl | CH₃ | t = 1.223 (MS [m/z]: 396.2) [B] 1H NMR see above |

-continued

I-ex

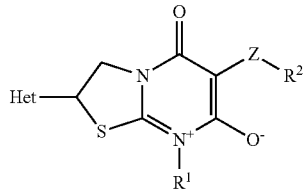

| Example No | Het | Z—R² | R¹ | Physicochemical data: HPLC-Retention [min] |
|---|---|---|---|---|
| 12 | 2-chloro-thiazol-5-yl | 4'-(2-methoxyphenyl)phenyl | CH₂CH₃ | t = 2.654 (MS [m/z]: 498.0) [C] |
| 13 | 2-chloro-thiazol-5-yl | 4'-(2-methoxyphenyl)phenyl | CH₃ | t = 2.468 (MS [m/z]: 484.0) [C] |
| 14 | 2-chloro-thiazol-5-yl | 2,4-dimethoxyphenyl | CH₃ | t = 1.744 (MS [m/z]: 430.0) [C] |
| 15 | 2-chloro-thiazol-5-yl | 3-(3-methylbenzyloxy)phenyl | CH₃ | t = 2.662 (MS [m/z]: 498.0) [C] |
| 16 | 2-chloro-thiazol-5-yl | 2-fluorophenyl | CH₃ | t = 1.852 (MS [m/z]: 396.0) [C] |
| 17 | 2-chloro-thiazol-5-yl | 4-isopropoxyphenyl | CH₃ | t = 2.188 (MS [m/z]: 422.0) [C] |
| 18 | 2-chloro-thiazol-5-yl | 2',4'-difluorobiphenyl | CH₃ | t = 2.589 (MS [m/z]: 490.0) [C] |
| 19 | 2-chloro-thiazol-5-yl | 4-(2-methoxyethoxy)phenyl | CH₃ | t = 1.849 (MS [m/z]: 452.0) [C] |

I-ex

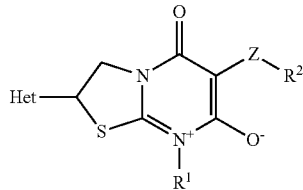

| Example No | Het | Z—R² | R¹ | Physicochemical data: HPLC-Retention [min] |
|---|---|---|---|---|
| 20 | (2-chloro-thiazol-5-yl) | (3-cyanophenyl) | CH₃ | t = 1.197 (MS [m/z]: 403.3) [B] |

HPLC Methods:
Method A:
Column: Phenomenex Kinetex 1.7 μm XB-C18 100A, 50×2.1 mm; MSD4/5 Shimadzu Nexera UHPLC+Shimadzu LCMS 20-20, ESI; Mobile Phase: A: water+0.1% TFA; B: acetonitrile: Temperature: 60° C.; Gradient: 5% B to 100% B in 1.50 min; 100% B 0.25 min; Flow: 0.8 ml/min to 1.0 ml/min in 1.51 min; MS method: ESI positive; Mass range (m/z): 100-700
Method B:
Column: YMC-PACK ODS-A, 50 mm*3.0 mm ID, 3 um 12 nm (BCIPL/COL/15/LC/019)
A=10 mM Amm. Formate (0.1% Formic Acid)
B=Acetonitrile (0.1% Formic Acid)
Flow=1.2 ml/min. Column oven: 40 C
Method C:
Column: Agilent Eclipse Plus C18, 50 mm*4.6 mm ID, 5 um
A=10 mM Amm. Formate (0.1% Formic Acid)
B=Acetonitrile (0.1% Formic Acid)
Flow=1.2 ml/min. Column oven: 30 C The biological activity of the compounds of formula (I) of the present invention can be evaluated in biological tests as described in the following.

General conditions: If not otherwise specified, most test solutions are to be prepared as follows:

The active compound is dissolved at the desired concentration in a mixture of 1:1 (vol:vol) distilled water:acetone. The test solution is prepared at the day of use.

Test solutions are prepared in general at concentrations of 2500 ppm, 1000 ppm, 500 ppm, 300 ppm, 100 ppm and 30 ppm (wt/vol).

1.) Green Peach Aphid (*Myzus persicae*)

a) For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compound C-1 at 2500 ppm showed over 75% mortality in comparison with untreated controls.

b) The active compounds were formulated by a Tecan liquid handler in 100% cyclohexa-none as a 10,000 ppm solution supplied in tubes. The 10,000 ppm solution was serially diluted in 100% cyclohexanone to make interim solutions. These served as stock solu-tions for which final dilutions were made by the Tecan in 50% acetone:50% water (v/v) into 10 or 20 ml glass vials. A nonionic surfactant (Kinetic®) was included in the solution at a volume of 0.01% (v/v).

The vials were then inserted into an automated electrostatic sprayer equipped with an atomizing nozzle for application to plants/insects.

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, compounds 1, 2, 3, 4, 5, 6, 7 and 8 at 2500 ppm showed over 75% mortality in comparison with untreated controls.

2.) Orchid *Thrips* (*Dichromothrips Corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

*Thrips* potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with about 20 adult *thrips*. The petri dishes were then covered with lids. All test arenas were held under continuous light and a temperature of about 28° C. for duration of the assay. After 3 days, the numbers of live *thrips* were counted on each flower, and along inner walls of each petri dish. The percent mortality was recorded 72 hours after treatment.

In this test, compounds C-1 and 8 at 500 ppm showed over 75% mortality in comparison with untreated controls.

3.) Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compound C-1 at 500 ppm showed over 75% mortality in comparison with untreated controls.

4.) Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compound C-1 at 500 ppm showed over 75% mortality in comparison with untreated controls.

5.) Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25+1° C. and about 75+5% relative humidity for 5 days. Egg and larval mortality was then visually assessed.

In this test, compounds 2, 3, 5, 8 at 2500 ppm showed over 75% mortality in comparison with untreated controls.

6.) Cowpea Aphid (*Aphis craccivora*)

The active compound is dissolved at the desired concentration in a mixture of 1:1 (vol:vol) distilled water: acetone. Surfactant (Kinetic® HV) is added at a rate of 0.01% (vol/vol). The test solution is prepared at the day of use.

Potted cowpea plants were colonized with approximately 30-50 aphids of various stages by manually transferring a leaf tissue cut from infested plant 24 hours before application. Plants were sprayed with the test solutions using a DeVilbiss® hand atom-izer at 20-30 psi (=1.38 to 2.07 bar) after the pest population has been checked. Treat-ed plants are maintained on light carts at about 25-26° C. Percent mortality was assessed after 72 hours.

In this test, compounds 1, 4, 5, 7, 8 at 500 ppm showed over 75% mortality in comparison with untreated controls.

7.) Cotton Aphid (*Aphis gossypii*) I

The active compounds were formulated by a Tecan liquid handler in 100% cyclohexa-none as a 10,000 ppm solution supplied in tubes. The 10,000 ppm solution was serially diluted in 100% cyclohexanone to make interim solutions. These served as stock solu-tions for which final dilutions were made by the Tecan in 50% acetone:50% water (v/v) into 10 or 20 ml glass vials. A nonionic surfactant (Kinetic®) was included in the solution at a volume of 0.01% (v/v).

The vials were then inserted into an automated electrostatic sprayer equipped with an atomizing nozzle for application to plants/insects.

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then main-tained in a growth room under fluorescent lighting in a 24-hr photoperiod at 25° C. and 20-40% relative humidity. Aphid mortality on the treated plants, relative to mortality on untreated control plants, was determined after 5 days.

In this test, compound 1 at 300 ppm showed over 75% mortality in comparison with untreated controls.

8.) Silverleaf Whitefly (*Bemisia argentifolii*)

The active compounds were formulated by a Tecan liquid handler in 100% cyclohexa-none as a 10,000 ppm solution supplied in tubes. The 10,000 ppm solution was serially diluted in 100% cyclohexanone to make interim solutions. These served as stock solu-tions for which final dilutions were made by the Tecan in 50% acetone:50% water (v/v) into 5 or 10 ml glass vials. A nonionic surfactant (Kinetic®) was included in the solution at a volume of 0.01% (v/v).

The vials were then inserted into an automated electrostatic sprayer equipped with an atomizing nozzle for application to plants/insects.

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was pla-ced into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding.

Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds 4 and 6 at 300 ppm showed over 75% mortality in comparison with untreated controls.

9.) Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23+1° C. and about 50+5% relative humidity for 5 days. Aphid mortality and fecundity was then visually assessed.

In this test, compounds 1, 2, 3, 4, 5, 6, 7 and 8 at 2500 ppm showed over 75% mortality in comparison with untreated controls.

The invention claimed is:

1. A substituted pyrimidinium compound of formula (Iaa):

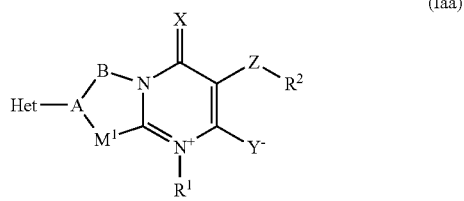

(Iaa)

wherein

X and Y are each independently O or S;

Z is a direct bond, O, S(O)$_m$, NR$^b$, C(R$^{aa}$R$^{aa}$)O, C(=X$^1$), C(=X$^1$)Y$^1$ or Y$^1$C(=X$^1$);

X$^1$ is O, S or NR$^b$;

Y$^1$ is O, S or NR$^c$;

A is CH;

B is CR'R";

M$^1$ is S(O)$_m$;

R' and R" are each independently H, halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, N=S(=O)$_p$R$^c$R$^c$, S(=O)$_o$(=NR$^b$)$_q$R$^c$, SF$_5$, OCN, SCN, Si(R$^d$)$_3$ or a three- to six-membered saturated, or partially unsaturated or aromatic carbo- or heterocyclic ring, which may contain 1 to 3 heteroatoms selected from N—(R$^c$)$_p$, O, and S which may be oxidized, and wherein the aforementioned groups and the carbo- or heterocyclic ring may be partially or fully substituted by R'", R'" is each independently halogen, C$_1$-C$_6$-alkyl, C$_1$-C$_6$-haloalkyl, C$_1$-C$_6$-alkoxy or C$_1$-C$_6$-haloalkoxy;
or R' and R" together form a group selected from =O, =S, =CR$^b$R$^c$, =NR$^c$, =NOR$^c$ and =NNR$^c$R$^c$;

Het is a three- to ten-membered heterocyclic ring or a seven- to eleven-membered heterocyclic ring system, each ring or ring system member selected from carbon atoms and up to 4 heteroatoms independently selected from up to 2 O, up to 2 S, and up to 4 N(R$^c$)$_p$, wherein up to 3 carbon atom ring members are independently selected from C(=O) and C(=S) and the sulfur atom ring members are independently selected from S(=O)$_o$(=NR$^b$)$_q$, each ring or ring system optionally substituted with up to 5 R$^a$;

o and q are each independently 0, 1 or 2, provided that the sum (o+q) is 0, 1 or 2 for each ring;

R$^1$ is hydrogen, C$_1$-C$_8$-alkyl, C$_2$-C$_8$-alkenyl, C$_2$-C$_8$-alkynyl, C$_3$-C$_{10}$-cycloalkyl, C$_4$-C$_{10}$-cycloalkenyl, C$_5$-C$_{14}$-cycloalkylcycloalkyl or R$^1$ may form a three- to eleven-membered saturated, partially unsaturated or aromatic carbo- or heterocyclic ring or ring system, which may contain 1 to 4 heteroatoms selected from N(R$^c$)$_p$, O, and S, wherein S may be oxidized, and wherein the aforementioned groups and the carbo- or heterocyclic ring system may be unsubstituted, partially or fully substituted by R$^a$; or R$^1$ is C(=O)R$^b$, C(=O)OR$^e$, NR$^b$R$^c$, C(=O)NR$^b$R$^c$, C(=S)NR$^b$R$^c$, SO$_2$NR$^b$R$^c$, OC(=O)R$^c$, OC(=O)OR$^e$, OC(=O)NR$^b$R$^c$, N(R$^c$)C(=O)R$^c$, N(R$^c$)C(=O)OR$^e$, N(R$^c$)C(=O)NR$^b$R$^c$, NR$^c$SO$_2$R$^b$, NR$^c$SO$_2$NR$^b$R$^c$, Si(R$^d$)$_3$, C(=NR$^c$)R$^c$, C(=NOR$^c$)R$^a$, C(=NNR$^b$R$^c$)R$^c$, C(=NN(C(=O)R$^b$)R$^c$)R$^c$, C(=NN(C=O)OR$^c$)(R$^c$)$_2$, S(=O)$_o$(=NR$^b$)$_q$R$^c$ or N=CR$^b$R$^c$;

R$^a$ is each independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, N=S(=O)$_p$R$^c$R$^c$, S(=O)$_o$(=NR$^b$)$_q$R$^c$, SF$_5$, OCN, SCN, Si(R$^d$)$_3$ or a three- to six-membered saturated, or partially unsaturated or aromatic carbo- or heterocyclic ring, which may contain 1 to 3 heteroatoms selected from N—(R$^c$)$_p$, O, and S which may be oxidized, and wherein the aforementioned groups and the carbo- or heterocyclic ring may be partially or fully substituted by R$^{aa}$, or two geminally bound groups R$^a$ together may form a group selected from =O, =S, =CR$^b$R$^c$, =NR$^c$, =NOR$^c$, and =NNR$^c$R$^c$;

R$^{aa}$ is each independently hydrogen, halogen, C$_1$-C$_6$-alkyl, C$_1$-C$_6$-haloalkyl, C$_1$-C$_6$-alkoxy or C$_1$-C$_6$-haloalkoxy;

R$^b$ is each independently hydrogen, C$_1$-C$_6$-alkyl, C$_1$-C$_6$-haloalkyl, C$_1$-C$_6$-alkoxy, C$_1$-C$_6$-haloalkoxy or a three- to six-membered saturated, or partially unsaturated or aromatic carbo- or heterocyclic ring, which may contain 1 to 3 heteroatoms selected from N(R$^c$)$_p$, O, and S, wherein S may be oxidized and which carbo- or heterocyclic ring may be partially or fully substituted by R$^{aa}$;

R$^c$ is each independently hydrogen, C$_1$-C$_4$-alkyl, C$_1$-C$_4$-haloalkyl, C$_1$-C$_4$-alkylcarbonyl, C$_1$-C$_6$ cycloalkyl, or a three- to six-membered saturated, partially unsaturated or aromatic carbo- or heterocyclic ring, which may contain 1 to 3 heteroatoms selected from N(R$^{aa}$)$_p$, O and S, wherein S may be oxidized and wherein the carbo- or heterocyclic ring may be partially or fully substituted by R$^{aa}$;

wherein two geminally bound groups R$^b$R$^b$, R$^c$R$^b$ or R$^c$R$^c$ together with the atom to which they are bound, may form a 3-, 4-, 5-, 6- or 7-membered saturated, partially unsaturated or aromatic carbo- or heterocyclic ring, which may contain 1 or 2 heteroatoms or heteroatoms groups selected from N, O, S, NO, SO and SO$_2$ and wherein the carbo- or heterocyclic ring may be partially or fully substituted by R$^{bb}$;

R$^{bb}$ is each independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, OR$^c$, NR$^b$R$^c$, NO$_2$, C(=O)(O)$_p$R$^c$, OC(=O)(O)$_p$R$^e$, C(=O)NR$^b$R$^c$, OC(=O)NR$^b$R$^c$, NR$^b$C(=O)(O)$_p$R$^e$, NR$^b$C(=O)NR$^b$R$^c$, C(=S)NR$^b$R$^c$, S(O)$_m$R$^b$, SO$_2$NR$^b$R$^c$, OSO$_2$R$^c$, OSO$_2$NR$^b$R$^c$, NR$^b$SO$_2$R$^c$, NR$^b$SO$_2$NR$^b$R$^c$, SF$_5$, OCN, SCN, Si(R$^d$)$_3$, C(=N(O)$_p$R$^b$)R$^b$, C(=NNR$^b$R$^c$)R$^b$, C(=NN(C(=O)O$_p$R$^d$)R$^b$)R$^b$, ON=CR$^b$R$^c$, ONR$^b$R$^c$, S(=O)$_o$(=NR$^b$)$_q$R$^c$, SO$_2$NR$^b$(=O)NR$^b$R$^c$, P(=X$^2$)R$^b$R$^c$, OP(=X$^2$)(O$_p$R$^c$)R$^b$, OP(=X$^2$)(OR$^c$)$_2$, N=CR$^b$R$^c$, RN$^b$N=CR$^b$R$^c$, NR$^b$-NR$^b$R$^c$, NR$^b$C(=S)NR$^b$R$^c$, NR$^b$C(—NR$^b$)NR$^b$R$^c$, NR$^b$NR$^b$C(=X$^2$)NR$^b$R$^c$, NR$^b$NR$^b$SO$_2$NR$^c$, or N=S(=O)$_p$R$^c$R$^c$ or two geminally bound groups R$^{bb}$ together may form a group selected from =O, =S, =CR$^b$R$^c$, =NR$^c$, =NOR$^c$, and =NNR$^c$R$^c$;

R$^d$ is each independently hydrogen, phenyl, C$_1$-C$_6$-alkyl, C$_2$-C$_6$-alkenyl, C$_2$-C$_6$-alkynyl, C$_3$-C$_8$-cycloalkyl, or C$_1$-C$_6$-alkoxyalkyl, wherein the above mentioned groups may be substituted by one or more halogen;

R$^e$ is each independently, C$_1$-C$_4$-alkyl, C$_1$-C$_4$-haloalkyl, C$_1$-C$_4$-alkylcarbonyl, C$_1$-C$_6$ cycloalkyl, or a three- to six-membered saturated, partially unsaturated or aromatic carbo- or heterocyclic ring, which may contain 1 to 3 heteroatoms selected from N(R$^{aa}$)$_p$, O and S, wherein S may be oxidized and wherein the carbo- or heterocyclic ring may be partially or fully substituted by $R^{aa}$;

m is 0, 1, or 2;

p is 0 or 1;

$R^2$ is H, halogen, CN, $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, wherein the aforementioned groups may be unsubstituted, partially, or fully substituted with $R^{2a}$, or $R^2$ may form a carbo- or heterocyclic three- to ten-membered ring or a seven- to eleven-membered ring system, which ring or ring system may be saturated, partially unsaturated, or aromatic, and which ring or ring system may contain 1 to 4 heteroatoms selected from $N(R^c)_p$, O and S, wherein S may be oxidized, and wherein the carbo- or heterocyclic ring or ring system may be unsubstituted, partially or fully substituted by $R^{2a}$;

with the proviso that if $R^2$ is halogen or CN, then Z is a direct bond;

$R^{2a}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^c$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^b$-$NR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, $N=S(=O)_pR^cR^c$, or a three- to six-membered saturated, or partially unsaturated or aromatic carbo- or heterocyclic ring, which may contain 1 to 3 heteroatoms selected from $N—(R^c)_p$, O and S, wherein S may be oxidized, and wherein the aforementioned groups and the carbo- or heterocyclic ring may be partially or fully substituted by $R^{2aa}$ or two geminally bound groups $R^{2a}$ together may form a group selected from =O, =S, $=CR^bR^c$, $=NR^c$, $=NOR^c$ and $=NNR^cR^c$;

$R^{2aa}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^c$, $C(=O)NR^bR^c$, $OC(=O)NR^bR^c$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^b$-$NR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$; or two geminally bound groups $R^{2aa}$ together may form a group selected from =O, =S,$=CR^bR^c$, $=NR^c$, $=NOR^c$ and $=NNR^cR^c$; and $X^2$ is independently O or S;

or a stereoisomer, or an agriculturally or veterinary acceptable salt or tautomer or N-oxide thereof.

2. The compound according to claim 1, or a stereoisomer, or an agriculturally or veterinary acceptable salt or tautomer or N-oxide thereof, wherein Het is selected from D-1 to D-56,

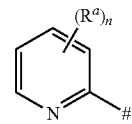
D-1

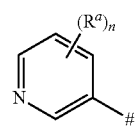
D-2

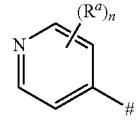
D-3

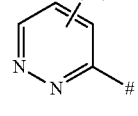
D-4

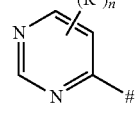
D-5

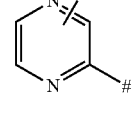
D-6

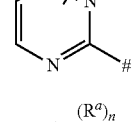
D-7

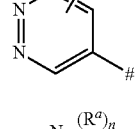
D-8

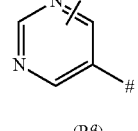
D-9

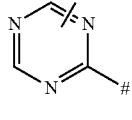
D-10

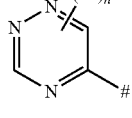
D-11

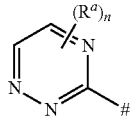
D-12

-continued
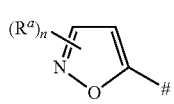 D-13
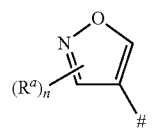 D-14
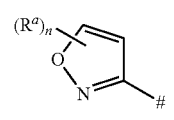 D-15
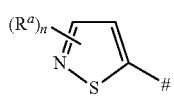 D-16
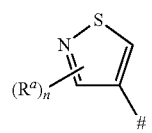 D-17
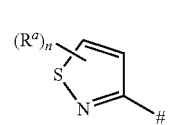 D-18
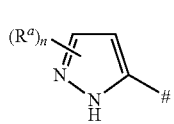 D-19
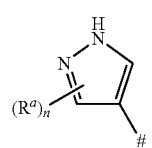 D-20
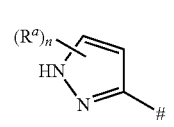 D-21
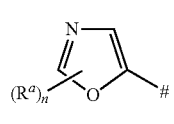 D-22
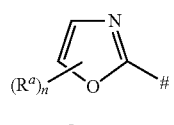 D-23
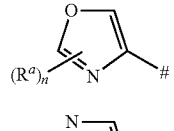 D-24
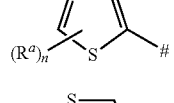 D-25
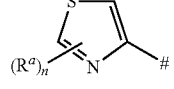 D-26
-continued
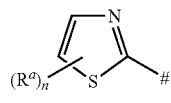 D-27
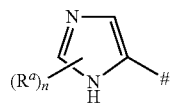 D-28
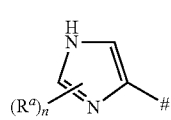 D-29
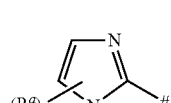 D-30
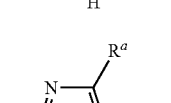 D-31
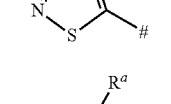 D-32
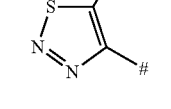 D-33
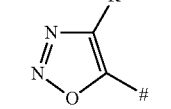 D-34
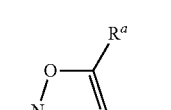 D-35
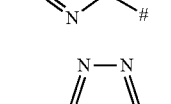 D-36
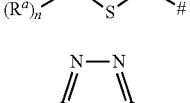 D-37
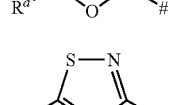 D-38
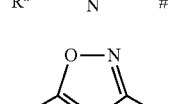 D-39
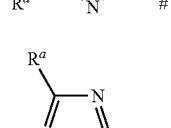

-continued

D-40 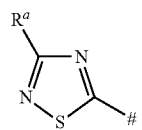

D-41 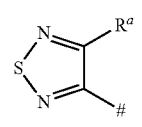

D-42 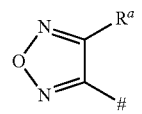

D-43 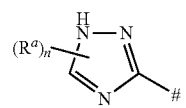

D-44 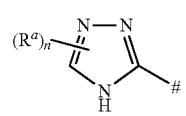

D-45 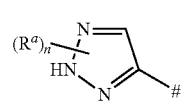

D-46 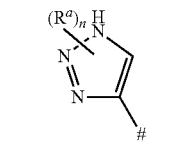

D-47 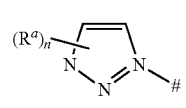

D-48 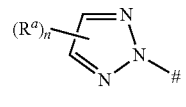

D-49 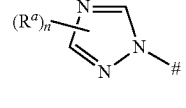

D-50 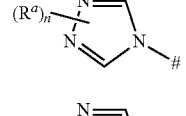

D-51 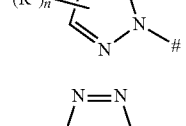

D-52 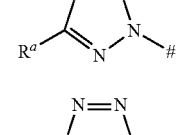

D-53 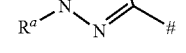

-continued

D-54 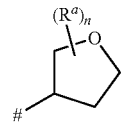

D-55 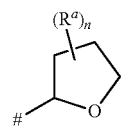

D-56 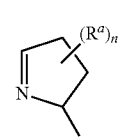

wherein
n is 0, 1, 2, 3 or 4;
$R^a$ has the meanings given for formula (Iaa) and
\# denotes the bond to A in formula (Iaa).

3. The compound according to claim 2, or a stereoisomer, or an agriculturally or veterinary acceptable salt or tautomer or N-oxide thereof, wherein Het is selected from structures D-2, D-9, D-22, D-25, D-28, D-29, D-54 and D-56, wherein
$R^a$ is halogen, $C_1$-$C_4$-haloalkyl, $C_1C_4$-alkoxy or $C_1$-$C_4$-alkylthio or phenyl,
n is 0, 1 or 2 and
\# denotes the bond to A in formula (Iaa).

4. The compound according to claim 1, or a stereoisomer, or an agriculturally or veterinary acceptable salt or tautomer or N-oxide thereof, wherein X and Y are O.

5. The compound according to claim 1, or a stereoisomer, or an agriculturally or veterinary acceptable salt or tautomer or N-oxide thereof, wherein
Z is a direct bond, and
$R^2$ is a six membered carbo- or heterocyclic ring, which ring may be unsubstituted, partially or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted by halogen, $C_1$-$C_6$-haloalkyl and/or $C_1$-$C_6$-haloalkoxy.

6. The compound according to claim 1, or a stereoisomer, or an agriculturally or veterinary acceptable salt or tautomer or N-oxide thereof, wherein
$R^1$ is $C_1$-$C_4$-alkyl, $C_3$-$C_6$-cycloalkyl, $C_2$-$C_4$-alkenyl, benzyl or phenyl, which groups may be partially or fully substituted by halogen or $C_1$-$C_4$-alkyl.

7. The compound according to claim 2, or a stereoisomer, or an agriculturally or veterinary acceptable salt or tautomer or N-oxide thereof, wherein
X and Y are each O;
$R^1$ is $CH_3$, $CH_2CH_3$, isopropyl, cyclopropyl, $CH_2CF_3$, phenyl, allyl or benzyl;
B is $CH_2$;
$R^2$ is phenyl which may be substituted by halogen, $C_1$-$C_6$-haloalkyl, $C_1$-$C_6$-haloalkoxy or phenyl;
Z is a direct bond and
Het is D-2, D-9, D-25 or D-56 and
$R^a$ is Cl, Br, F, $SCH_3$, $CF_3$, $OCH_3$ or phenyl.

8. A compound of the formula I-ex:

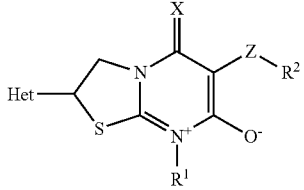

I-ex in which the substituents Het, Z—R² and R¹ are defined as follows:
| Compound No | Het | Z—R² | R¹ |
|---|---|---|---|
| 1 | 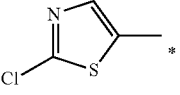 | 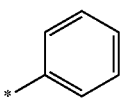 [SMILES: *c1ccccc1] | CH₃ |
| 2 | 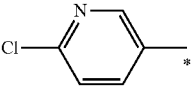 | 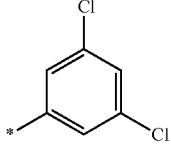 | CH₃ |
| 3 | 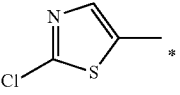 | 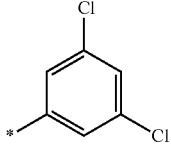 | CH₃ |
| 4 | 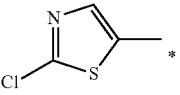 | 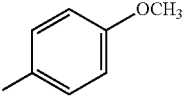 | CH₃ |
| 5 | 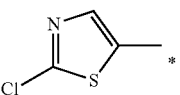 | 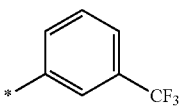 | CH₃ |
| 6 | 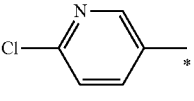 | 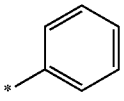 [SMILES: *c1ccccc1] | CH₃ |
| 7 | 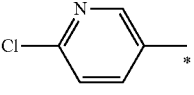 | 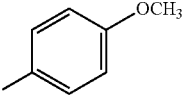 | CH₃ |
| 8 | 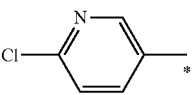 | 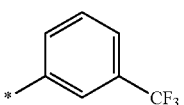 | CH₃ |
| 9 | 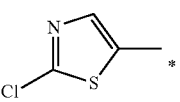 | 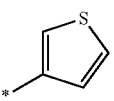 | CH₃ |
| 10 | 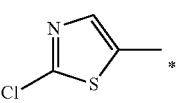 | 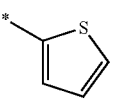 | CH₃ |
| 11 | 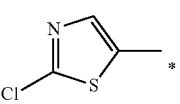 | 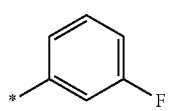 [SMILES: *c1cccc(F)c1] | CH₃ |
| 12 | 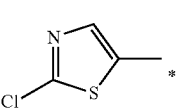 | 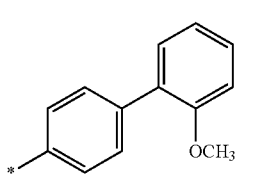 | CH₂CH₃ |

-continued

| Compound No | Het | Z—R² | R¹ |
|---|---|---|---|
| 13 | 2-Cl-thiazol-5-yl | 4'-(2-OCH₃)-biphenyl | CH₃ |
| 14 | 2-Cl-thiazol-5-yl | 2,4-di(OCH₃)-phenyl | CH₃ |
| 15 | 2-Cl-thiazol-5-yl | 3-(3-methylphenoxymethyl)-phenyl | CH₃ |
| 16 | 2-Cl-thiazol-5-yl | 2-F-phenyl | CH₃ |
| 17 | 2-Cl-thiazol-5-yl | 4-isopropoxy-phenyl | CH₃ |
| 18 | 2-Cl-thiazol-5-yl | 4'-(2,4-diF)-biphenyl | CH₃ |
| 19 | 2-Cl-thiazol-5-yl | 4-(2-methoxyethoxy)-phenyl | CH₃ |
| 20 | 2-Cl-thiazol-5-yl | 3-CN-phenyl | CH₃ | or a stereoisomer, or an agriculturally or veterinary acceptable salt or tautomer or N-oxide thereof.

9. A mixture comprising at least one compound according to claim 1, or a stereoisomer, or an agriculturally or veterinary acceptable salt or tautomer or N-oxide thereof, and at least one further pesticide.

10. A composition comprising at least one compound according to claim 1, or a stereoisomer, or an agriculturally or veterinary acceptable salt or tautomer or N-oxide thereof, and at least one of an inert liquid carrier and a solid carrier.

11. A method for at least one of protecting crops, plants, plant propagation material and growing plants from attack or infestation by invertebrate insects comprising contacting the crops, plants, plant propagation material and growing plants, or soil, material, surface, space, area or water in which the crops, plants, plant propagation material is stored or the plant is growing, with a pesticidally effective amount of at least one compound according to claim 1, or a stereoisomer, or an agriculturally or veterinary acceptable salt or tautomer or N-oxide thereof.

12. A method for combating or controlling invertebrate insects, which method comprises contacting said insects or their food supply, habitat or breeding grounds with a pesticidally effective amount of at least one compound as defined in claim 1, or a stereoisomer, or an agriculturally or veterinary acceptable salt or tautomer or N-oxide thereof.

13. A non-therapeutic method for at least one of treating animals infested or infected by parasites, preventing animals from getting infected or infested by parasites, and protecting animals against infestation or infection by parasites which comprises at least one of orally, topically and parenterally administering or applying to the animals a parasiticidally effective amount of at least one compound according to claim 1, or a stereoisomer, or an agriculturally or veterinary acceptable salt or tautomer or N-oxide thereof, wherein the parasite is an insect.

14. A seed comprising a compound according to claim 1, or a stereoisomer, or an agriculturally or veterinary acceptable salt or tautomer or N-oxide thereof, in an amount of from 0.1 g to 10 kg per 100 kg of seed.

\* \* \* \* \*